(12) United States Patent
Nakayashiki et al.

(10) Patent No.: US 8,227,624 B2
(45) Date of Patent: Jul. 24, 2012

(54) AROMATIC SULFONIUM SALT COMPOUND

(75) Inventors: Tetsuyuki Nakayashiki, Tokyo (JP); Kentaro Kimura, Tokyo (JP)

(73) Assignee: Adeka Corporation, Tokyo (JP)

( * ) Notice: Subject to any disclaimer, the term of this patent is extended or adjusted under 35 U.S.C. 154(b) by 353 days.

(21) Appl. No.: 12/672,182

(22) PCT Filed: Aug. 4, 2008

(86) PCT No.: PCT/JP2008/063952
§ 371 (c)(1),
(2), (4) Date: Feb. 4, 2010

(87) PCT Pub. No.: WO2009/020089
PCT Pub. Date: Feb. 12, 2009

(65) Prior Publication Data
US 2011/0152540 A1   Jun. 23, 2011

(30) Foreign Application Priority Data
Aug. 7, 2007   (JP) .................................. 2007-205876

(51) Int. Cl.
*C07D 333/76* (2006.01)
*C07C 381/12* (2006.01)

(52) U.S. Cl. ................ 549/43; 568/77; 568/75; 568/34; 558/268; 558/46; 560/104

(58) Field of Classification Search .................. 560/104; 558/268, 46; 568/77, 75, 34; 549/43
See application file for complete search history.

(56) References Cited

U.S. PATENT DOCUMENTS

| | | | |
|---|---|---|---|
| 5,159,088 A | 10/1992 | Schwalm | |
| 2006/0055088 A1* | 3/2006 | Nakayashiki et al. | 264/425 |

FOREIGN PATENT DOCUMENTS

| | | |
|---|---|---|
| JP | 3-148256 | 6/1991 |
| JP | 06-271532 | 9/1994 |
| JP | 07-126313 | 5/1995 |
| JP | 2003-192665 | 7/2003 |
| JP | 2004-217551 | 8/2004 |
| JP | 2004-323704 A | 11/2004 |
| JP | 2006-008586 A | 1/2006 |
| JP | 2007-091628 | 4/2007 |
| WO | WO-2004/029037 | 4/2004 |

* cited by examiner

*Primary Examiner* — Joseph Kosack
*Assistant Examiner* — Matthew Coughlin

(74) *Attorney, Agent, or Firm* — Birch, Stewart, Kolasch & Birch, LLP

(57) ABSTRACT

A photoacid generator which can generate an acid efficiently when energy was absorbed, is excellent in the developing property and can form fine patterns, and a cationic polymerization initiator excellent in curability are provided; and a resist composition and a cationically polymerizable composition using them are provided.
An aromatic sulfonium salt compound represented by the General Formula (I) below:

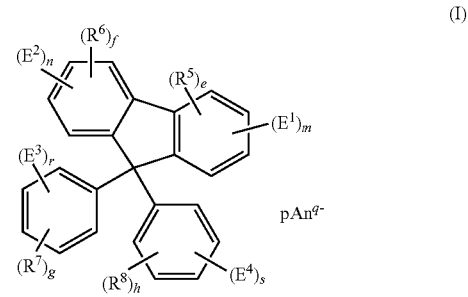

(wherein each of $E^1$ to $E^4$ independently represents a substituent represented by the General Formula (II) below or the General Formula (III) below).

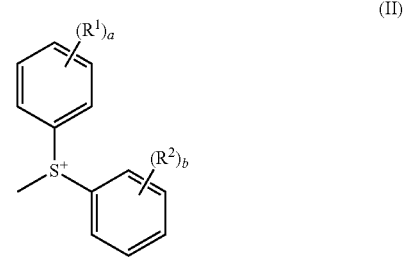

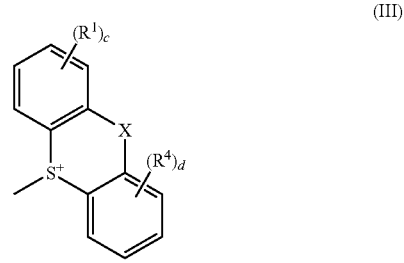

Preferably, in the General Formula (I), r and s are 0; m and n are 0; or n and r are 0, and more preferably, one of m and s in the General Formula (I) is 1.

16 Claims, No Drawings

AROMATIC SULFONIUM SALT COMPOUND

TECHNICAL FIELD

The present invention relates to a novel aromatic sulfonium salt compound (hereinafter also referred to as "compound"), more particularly, an aromatic sulfonium salt compound; a photoacid generator and a cationic polymerization initiator using it; and a resist composition and a cationically polymerizable composition containing them.

BACKGROUND ART

Sulfonium salt compounds are substances which generate acids when an energy line such as light is radiated thereto, and used for: photoacid generators in resist compositions for photolithography used for formation of electronic circuits such as semiconductors; and for cationic polymerization initiators in photo polymerizable compositions such as resin compositions for stereolithography, paints, coatings and adhesives.

For example, in Patent Documents 1 to 3, sulfonium salt compounds useful as photoacid generators are described, and also disclosed are cationic polymerization photoinitiators of epoxy resin using these photoacid generators, and photo polymerizable compositions using them.

Patent Document 1: Japanese Unexamined Patent Application Publication No. 7-126313

Patent Document 2: Japanese Unexamined Patent Application Publication No. 2004-217551

Patent Document 3: Japanese Unexamined Patent Application Publication No. 2007-91628

DISCLOSURE OF THE INVENTION

Problems to be Solved by the Invention

However, a preferred performance could not be obtained sufficiently with the aromatic sulfonium salt compounds described in the above-described Patent Documents 1-3. Recently, wavelengths of energy sources are becoming shorter and fine patterning are demanded, so that a photoacid generator which has a good acid generation efficiency and is excellent in the developing property, and a cationic polymerization initiator excellent in curability have been desired, and a compound effective for such uses has been demanded.

Thus, the present invention aims to provide a photoacid generator which can generate an acid efficiently when energy was absorbed, is excellent in the developing property and can form fine patterns, and a cationic polymerization initiator excellent in curability; and to provide a resist composition and a cationically polymerizable composition using them.

Means for Solving the Problems

The present inventors intensively studied for solving the above-described problems to discover a novel aromatic sulfonium salt compound having a prescribed structure and to discover that a performance superior to those of conventional materials can be obtained by using this as a photoacid generator and a cationic polymerization initiator, thereby completing the present invention.

That is, the aromatic sulfonium salt compound of the present invention is represented by the General Formula (I) below:

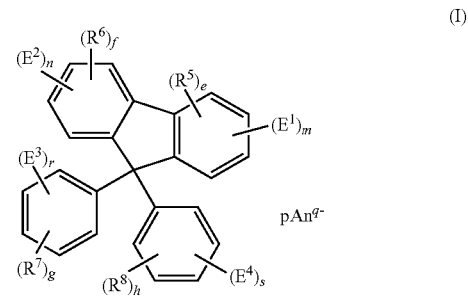

(wherein each of $E^1$ to $E^4$ independently represents a substituent represented by the General Formula (II) below or the General Formula (III) below:

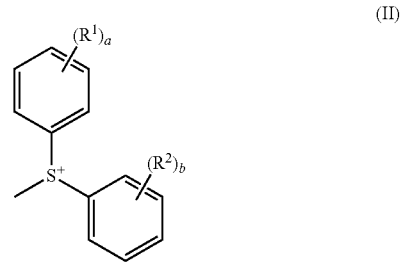

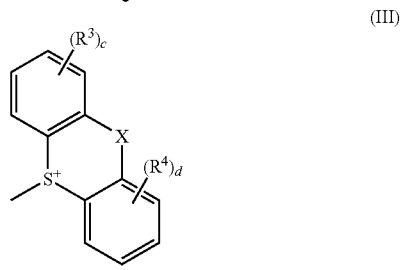

(wherein each of $R^1$ to $R^4$ independently represents hydroxyl, mercapto, a halogen atom, nitro, cyano, $C_1$-$C_{18}$ alkyl, $C_6$-$C_{20}$ aryl, $C_7$-$C_{20}$ arylalkyl, —OSi$R^{21}R^{22}R^{23}$ or —OP(=O)$R^{24}R^{25}$, wherein each of $R^{21}$ to $R^{25}$ independently represents $C_1$-$C_{18}$ alkyl, $C_6$-$C_{20}$ aryl or $C_7$-$C_{20}$ arylalkyl, wherein methylene groups in the above-described alkyl and arylalkyl are optionally interrupted by —O—, —CO—, —COO—, —COO—, —OCOO—, —S—, —SO—, —SO$_2$— or —SO$_3$—, and each hydrogen atom in the alkyl, aryl and arylalkyl is optionally substituted with a halogen atom; each of a and b represents an integer of 0 to 5 and each of c and d represents an integer of 0 to 4, with the proviso that in cases where each of a to d represents a number of not less than 2, its plurality of substituents represented by $R^1$ to $R^4$ are optionally the same or different; and X represents a direct bond, an oxygen atom, a sulfur atom, $CR^9R^{10}$, $NR^{11}$ or carbonyl; each of $R^9$ to $R^{11}$ represents a hydrogen atom, $C_1$-$C_{18}$ alkyl, $C_6$-$C_{20}$ aryl or $C_7$-$C_{20}$ arylalkyl); each of m, n, r and s independently represents 0 or 1 with the proviso that at least one of m and s is 1; each of $R^5$ to $R^8$ independently represents the same group as $R^1$ to $R^4$; An$^{q-}$ represents an anion having the valence of q (q represents 1 or 2); and p represents 1 or 2 which is a coefficient to maintain the neutrality of the charge).

The aromatic sulfonium salt compound of the present invention is preferably one wherein, in the General Formula (I), r and s are 0, m and n are 0, or n and r are 0.

In the aromatic sulfonium salt compound of the present invention, $An^{q-}$ is preferably a monovalent anion which is any group selected from the group consisting of a hexafluoroantimonate ion, hexafluorophosphate ion, hexafluoroarsenate ion, tetrafluoroborate ion, hexachloroantimonate ion, perchlorate ion, trifluoromethanesulfonate ion, methanesulfonate ion, fluorosulfonate ion, difluorophosphate ion, p-toluenesulfonate ion, camphorsulfonate ion, nonafluorobutanesulfonate ion, hexadecafluorooctanesulfonate ion, tetraarylborate ion and organic fluorosulfoneimide ion, among which a trifluoromethanesulfonate ion and a nonafluorobutanesulfonate ion are more preferred.

The aromatic sulfonium salt compound of the present invention is preferably one wherein each of $E^1$ to $E^4$ in the General Formula (I) is a group represented by the General Formula (II), and both g and h in the General Formula (I) are more preferably 1.

The aromatic sulfonium salt compound of the present invention is preferably one wherein at least one of $R^1$ to $R^8$ in the General Formulae (I) to (III) is hydroxyl, more preferably not less than 4 of $R^1$ to $R^8$ are hydroxyl.

In the present invention, an aromatic sulfonium salt compound wherein $R^1$, $R^2$, $R^7$ and $R^8$ are hydroxyl and a, b, g and h are 1 in the General Formulae (I) to (III) is preferred.

The photoacid generator of the present invention comprises the aromatic sulfonium salt compound.

The resist composition of the present invention comprises the photoacid generator.

The cationic polymerization initiator of the present invention comprises the aromatic sulfonium salt compound.

The cationically polymerizable composition of the present invention comprises the cationic polymerization initiator.

Effect of the Invention

The aromatic sulfonium salt compound of the present invention absorbs an energy line efficiently and is activated, to act as an excellent photoacid generator. Therefore, a photoresist of a photo polymerizable composition containing it has a high sensitivity and a high resolution. Further, since the aromatic sulfonium salt compound of the present invention can be obtained as crystals, it can be easily handled when used, and can be highly purified by recrystallization purification, so that a highly pure and highly sensitive photoacid generator free from impurities can be provided for uses such as microprocessing including photolithography and production of electronic parts, whose performances are largely affected by contamination of impurities.

Further, the sulfonium salt compound of the present invention is useful also as a cationic polymerization initiator, and by using this, a cationically polymerizable composition excellent in curability can be obtained.

BEST MODE FOR CARRYING OUT THE INVENTION

Preferred embodiments of the present invention will be described more concretely.

In the above-described General Formulae (I) to (III), examples of the halogen atoms represented by $R^1$ to $R^8$ and the halogen atoms which optionally substitute hydrogen atoms of alkyl, aryl and arylalkyl include fluorine, chlorine, bromine and iodine.

Methylene groups in the alkyl and arylalkyl represented by $R^1$ to $R^8$ are optionally interrupted by —O—, —CO—, —COO—, —OCO—, —OCOO—, —S—, —SO—, —SO$_2$— or —SO$_3$—, and alkylene moieties of these alkyl and arylalkyl are optionally interrupted by a double bond or triple bond.

Specific examples of the substituents represented by the above-described $R^1$ to $R^8$ include alkyl groups such as methyl, ethyl, propyl, isopropyl, butyl, isobutyl, t-butyl, pentyl, isopentyl, t-pentyl, neopentyl, hexyl, isohexyl, heptyl, octyl, 2-ethylhexyl, nonyl, decyl, undecyl, dodecyl, tridecyl, isotridecyl, myristyl, palmityl, stearyl, cyclopropyl, cyclohexyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, camphor-10-yl, vinyl, allyl, isopropenyl, 1-propenyl, 2-methoxy-1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, methoxymethyl, methoxyethoxymethyl, methylthiomethyl, ethoxyethyl, butoxymethyl, t-butylthiomethyl, 4-pentenyloxymethyl, trichloroethoxymethyl, bis(2-chloroethoxy)methyl, methoxycyclohexyl, 1-(2-chloroethoxy)ethyl, methoxyethyl, 1-methyl-1-methoxyethyl, ethyldithioethyl, trimethylsilylethyl, t-butyldimethylsilyloxymethyl, 2-(trimethylsilyl)ethoxymethyl, t-butoxycarbonylmethyl, ethyloxycarbonylmethyl, ethylcarbonylmethyl, t-butoxycarbonylmethyl, acryloyloxyethyl, methacryloyloxyethyl, 2-methyl-2-adamantyloxycarbonylmethyl and acetylethyl; aryl groups such as phenyl, 1-naphthyl, 2-naphthyl, anthracene-1-yl, phenanthrene-1-yl, o-tolyl, m-tolyl, p-tolyl, 4-vinylphenyl, ethylphenyl, propylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t-amylphenyl, cyclohexylphenyl, biphenylyl, 2,4,5-trimethylphenyl, 9-fluorenyl, 4-chlorophenyl, 3,4-dichlorophenyl, 4-trichlorophenyl, 4-trifluorophenyl, fluorophenyl, trifluoromethylphenyl, pentafluorophenyl, heptafluoro-p-tolyl, 4-formylphenyl, 4-nitrophenyl, ethoxynaphthyl, 4-fluoromethylphenyl, 4-methoxyphenyl and 2,4-dinitrophenyl; arylalkyl groups such as benzyl, methylbenzyl, dimethylbenzyl, trimethylbenzyl, phenylbenzyl, diphenylmethyl, triphenylmethyl, 2-phenylethyl, 2-phenylpropyl, styryl, cinnamyl, fluorobenzyl, chlorobenzyl, bromobenzyl, cyanobenzyl, dichlorobenzyl, methoxybenzyl, dimethoxybenzyl, benzyloxymethyl, methoxybenzyloxymethyl, 1-methyl-1-benzyloxyethyl, 1-methyl-1-benzyloxy-2-fluoroethyl, guaiacolmethyl, phenoxymethyl, phenylthiomethyl, nitrobenzyl, dinitrobenzhydryl, dibenzosuberyl, (phenyldimethylsilyl)methoxymethyl, phenylsulfonylethyl, triphenylphosphonioethyl, triphenylmethoxymethyl, phenacyl and bromophenacyl; alkoxy groups represented by RO—, having, as R, the above-described alkyl, aryl or arylalkyl group, or a heterocyclic group such as tetrahydropyranyl, 3-bromotetrahydropyranyl, tetrahydrothiopyranyl, methoxytetrahydropyranyl, methoxytetrahydrothiopyranyl, 4-methoxytetrahydrothiopyrane-S,S-dioxide-4-yl, 1-[(2-chloro-4-methyl)phenyl]-4-methoxypiperidine-4-yl, 1,4-dioxane-2-yl, tetrahydrofuranyl, tetrahydrothiofuranyl, 2,3,3a,4,5,6,7,7a-octahydro-7,8,8-trimethyl-4,7-methanobenzofuran-2-yl, 2-pyridylmethyl, 4-pyridylmethyl, 3-picoline-N-oxide-2-yl-methyl, 1,3-benzodithiolanyl, benzisothiazolin-S,S-dioxide-3-yl and tetrafluoro-4-pyridyl; acyl groups represented by RCO—; ester groups represented by RCOO— or ROCO—; carbonate groups represented by ROCOO—; sulfanyl groups represented by RS—; sulfinyl groups represented by RSO—; sulfonyl groups represented by $RSO_2$—; sulfonate ester groups represented by $RSO_3$—; formyl group; carboxyl group; formyloxy group; sulfo group; silyloxy groups such as trimethylsilyloxy, triethylsilyloxy, tripropylsilyloxy, dimethylpropylsilyloxy, diethylpropylsilyloxy, dimethyl(1,1,2,2-tetramethyl)ethylsilyloxy, butyldimethylsilyloxy, butyldiphenylsilyloxy, tribenzylsilyloxy, trixylylsilyloxy, triphenylsilyloxy, diphenylmethylsilyloxy and butylmethoxyphenylsilyloxy; substituted phosphoryloxy groups such as dimethylphosphoryloxy, diethylphosphoryloxy and diphenylphosphoryloxy; benzylthiocarbonate; and methyldithiocarbonate.

Among the above-described compounds, in the above formulae, those wherein at least one of $R^1$ to $R^8$ is hydroxyl are preferred for their excellent developing properties, and those wherein not less than 4 of $R^1$ to $R^8$ are hydroxyl are more preferred. Further, compounds wherein, in the above formulae, each of $R^1$, $R^2$, $R^7$ and $R^8$ is hydroxyl and each of a, b, g and h is 1 are especially preferred.

The aromatic sulfonium salt compound of the present invention is preferably one wherein, in the above-described General Formula (I), r and s are 0, m and n are 0, or n and r are 0 since it can be easily produced, and ones wherein, in the General Formula (I), the sum of m and s is 1 are more preferred.

Further, the aromatic sulfonium salt compound of the present invention is preferably one wherein each of $E^1$ to $E^4$ in the General Formula (I) is a group represented by the General Formula (II) in terms of its solubility or in that its structure may be easily changed, and both g and h in the General Formula (I) are more preferably 1.

In the General Formula (I), $An^{q-}$ represents an anion having the valence of q (q is 1 or 2), and specific examples thereof include, as monovalent anions ($An^-$), halogen anions such as chloride ion, bromide ion, iodide ion and fluoride ion; inorganic anions such as perchlorate ion, chlorate ion, thiocyanate ion, hexafluorophosphate ion, hexafluoroantimonate ion and tetrafluoroborate ion; organic sulfonate anions such as benzenesulfonate ion, toluenesulfonate ion, trifluoromethanesulfonate ion, diphenylamine-4-sulfonate ion, 2-amino-4-methyl-5-chlorobenzenesulfonate ion, 2-amino-5-nitrobenzenesulfonate ion and N-alkyl(or aryl)diphenylamine-4-sulfonate ion; organic phosphate anions such as octyl phosphate ion, dodecyl phosphate ion, octadecyl phosphate ion, phenyl phosphate ion, nonylphenyl phosphate ion and 2,2'-methylenebis(4,6-di-t-butylphenyl)phosphonate ion; bistrifluoromethylsulfonylimide ion; bisperfluorobutanesulfonylimide ion; perfluoro-4-ethylcyclohexanesulfonate ion; and tetrakis (pentafluorophenyl)borate ion; and as divalent anions ($An^{2-}$), benzenedisulfonate ion and naphthalenedisulfonate ion. Among these, hexafluoroantimonate ion, hexafluorophosphate ion, hexafluoroarsenate ion, tetrafluoroborate ion, hexachloroantimonate ion, perchlorate ion, trifluoromethanesulfonate ion, methanesulfonate ion, fluorosulfonate ion, difluorophosphate ion, p-toluenesulfonate ion, camphorsulfonate ion, nonafluorobutanesulfonate ion, hexadecafluorooctanesulfonate ion, organic fluorosulfoneimide ion and tetraarylborate ion and the like are preferred in view of their production, and further among these, trifluoromethanesulfonate ion and nonafluorobutanesulfonate ion are more preferred in view of cost, and safety and health.

Specific examples of the tetraarylborate ion include tetraphenylborate ion and compounds wherein at least one hydrogen atom of its phenyl group is substituted with alkyl, a halogen atom, halogenated alkyl, hydroxyalkyl, alkoxyl, phenyl or alkoxycarbonyl, and preferred examples thereof include tetrakis(pentafluorophenyl)borate ion, tetrakis(4-fluorophenyl)borate ion and tetraphenylborate ion. Specific examples of the organic fluorosulfoneimide ion include bis (trifluoromethanesulfone)imide ion, bis(pentafluoroethanesulfone)imide ion, bis(heptafluoropropanesulfone)imide ion, bis(nonafluorobutanesulfone)imide ion, bis(undecafluoropentanesulfone)imide ion, bis(pentadecafluoroheptanesulfone)imide ion, bis(tridecafluorohexanesulfone)imide ion, bis(heptadecafluorooctanesulfoneimide) ion, (trifluoromethanesulfone)(nonafluorobutanesulfone)imide ion and (methanesulfone)(trifluoromethanesulfone)imide ion.

Examples of the cation of the aromatic sulfonium salt compound of the present invention include the compounds below.

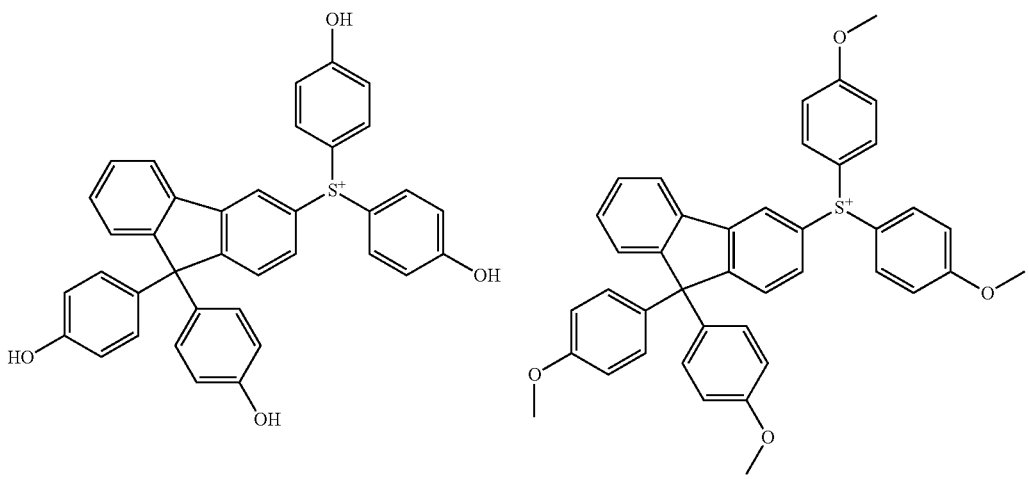

7
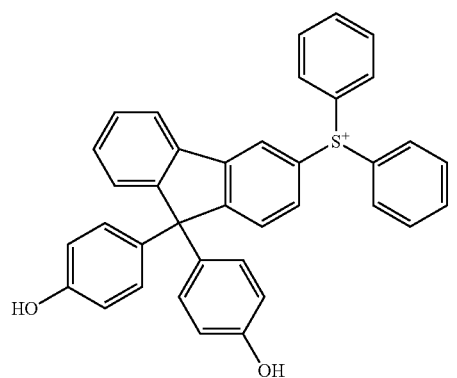
8
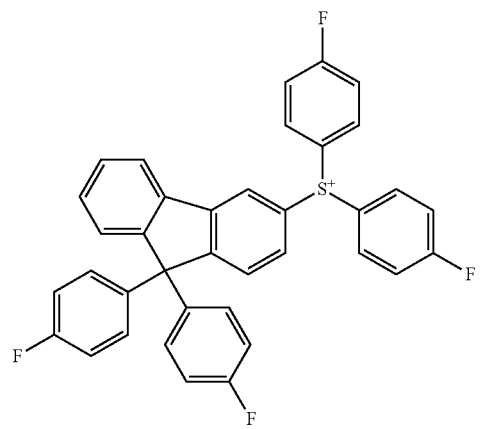
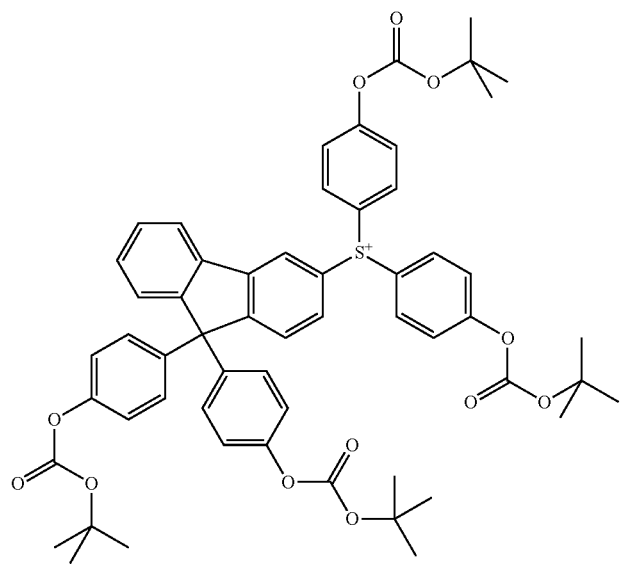
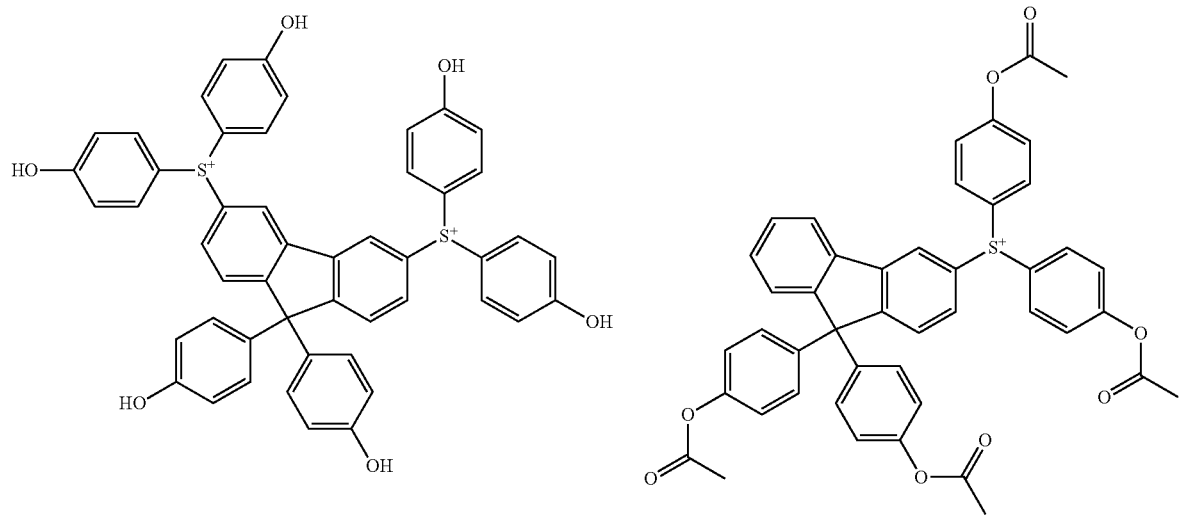

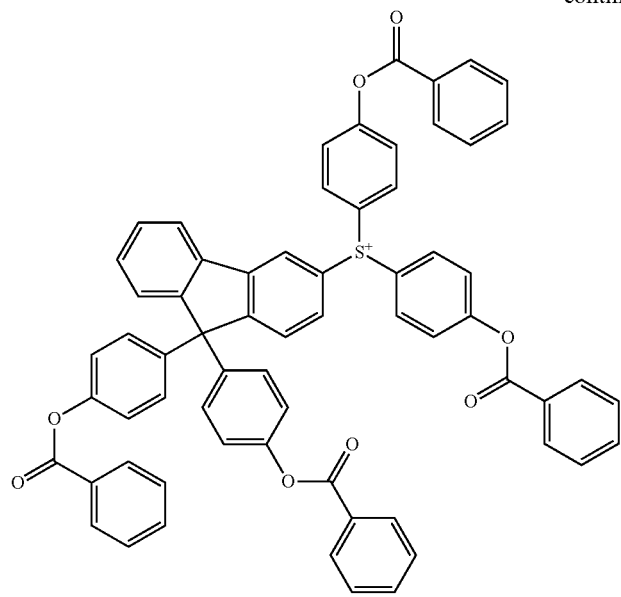
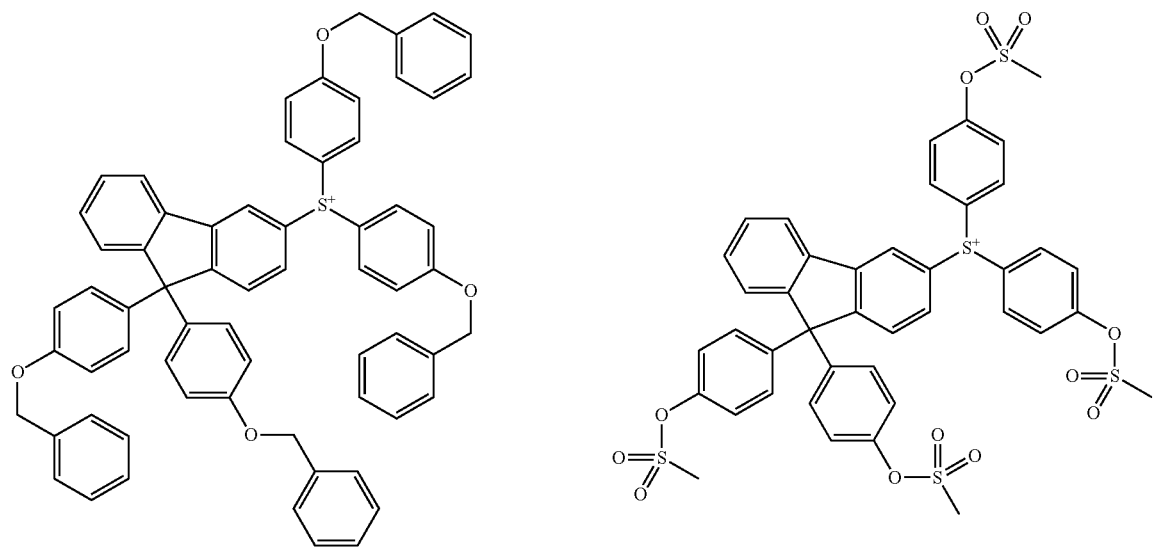
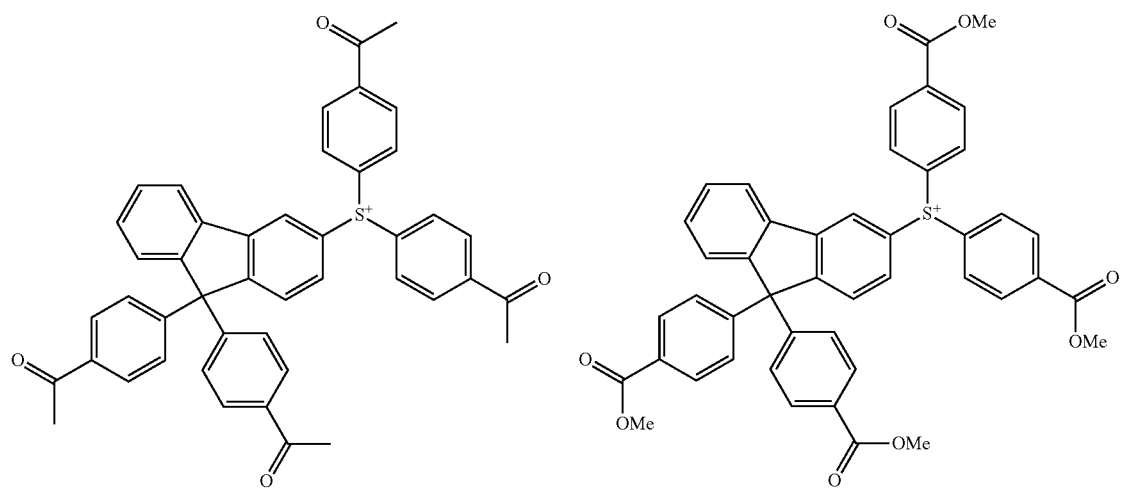

11 12
-continued
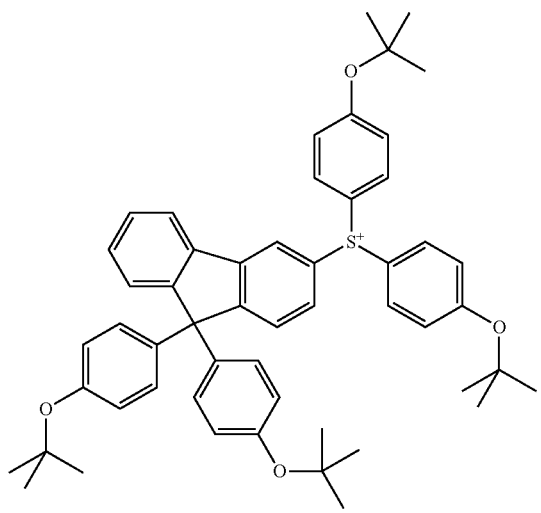
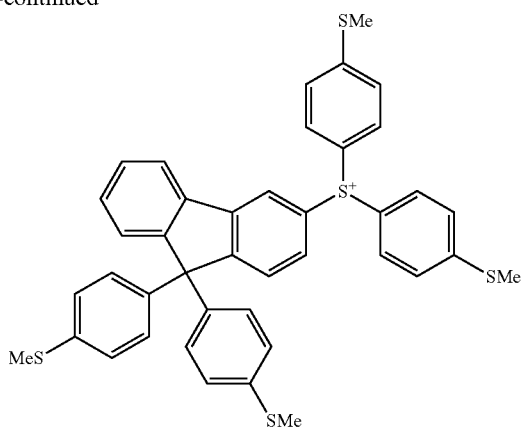
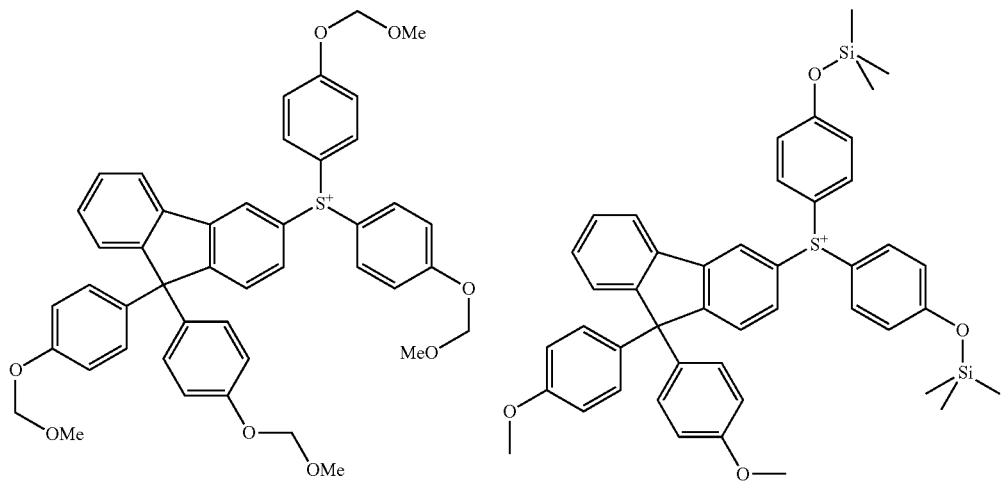
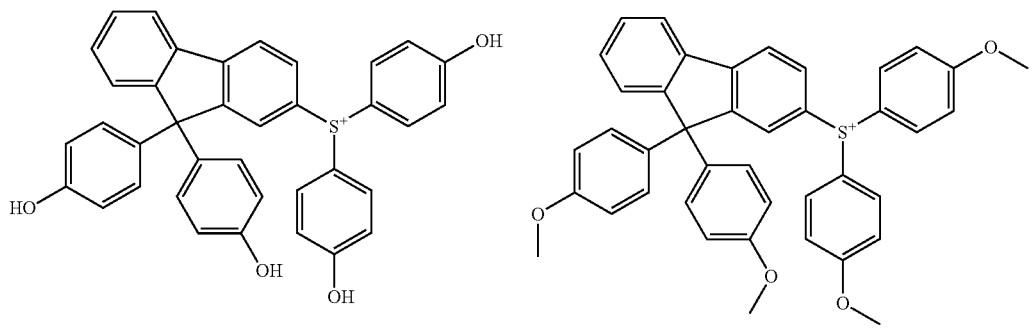
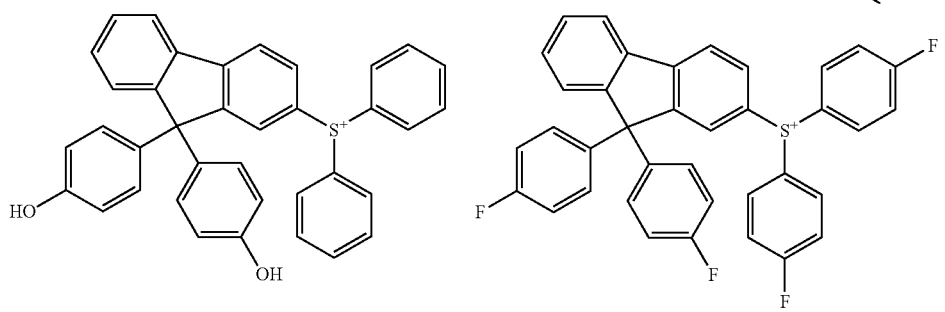

-continued
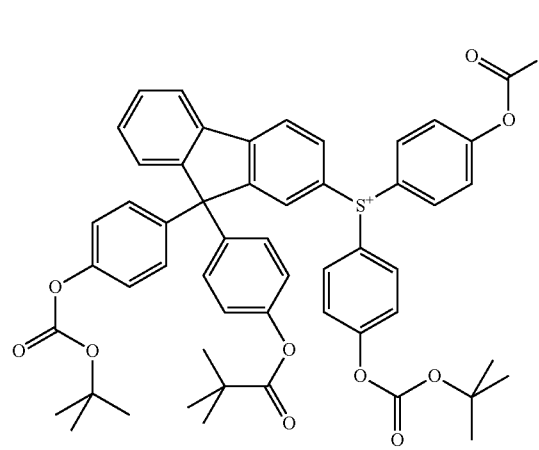
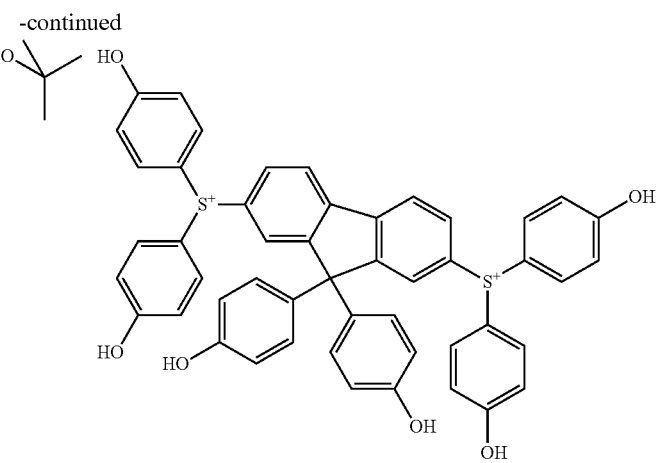
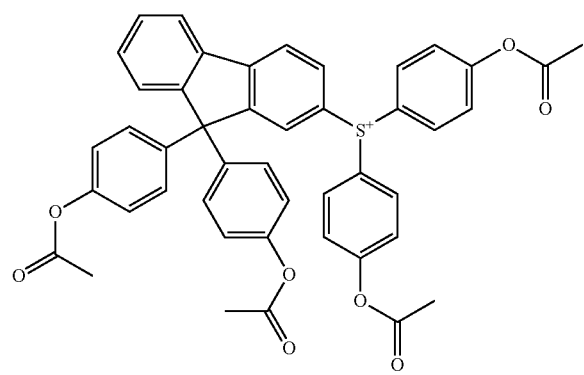
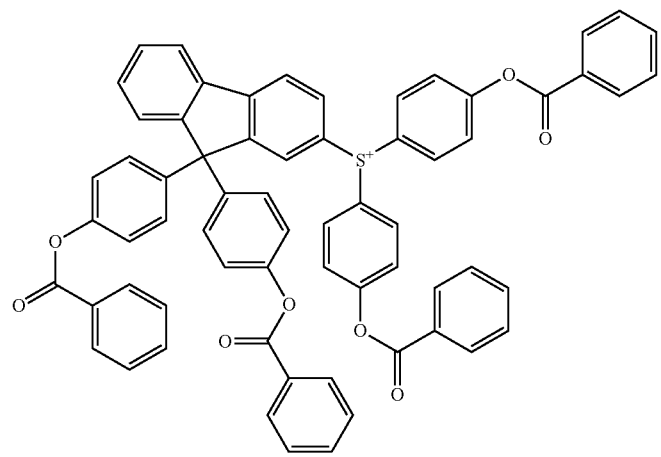
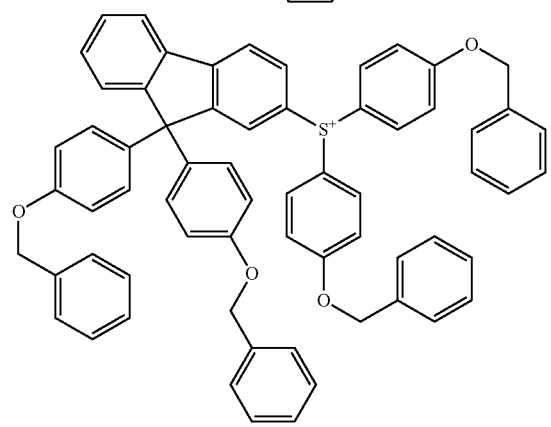
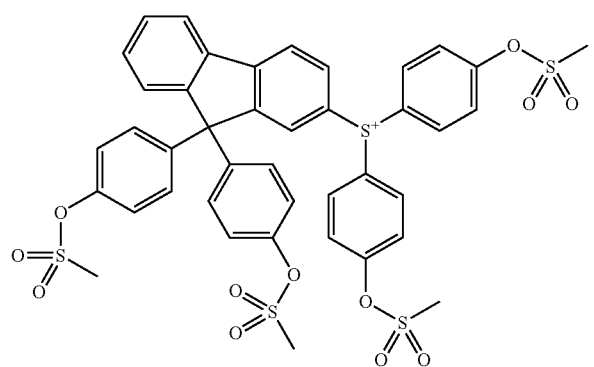

-continued
15
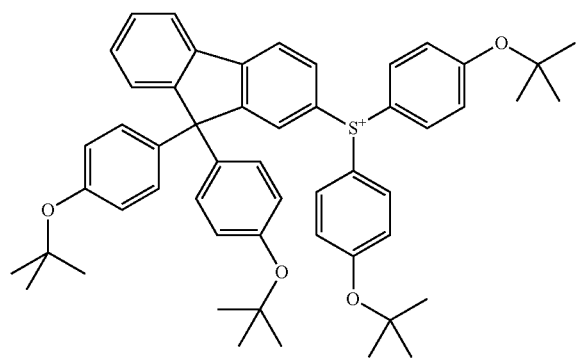
16
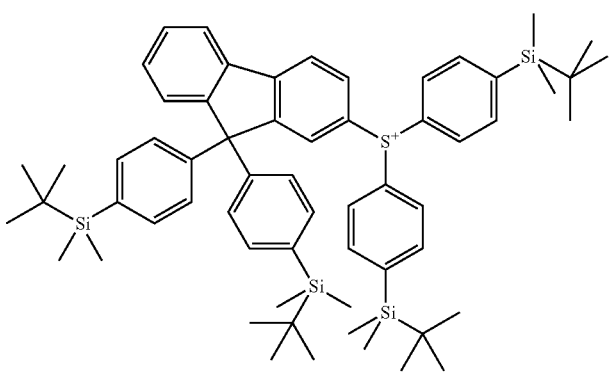
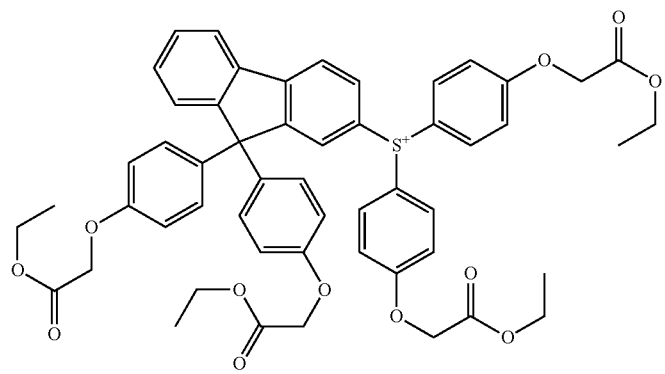
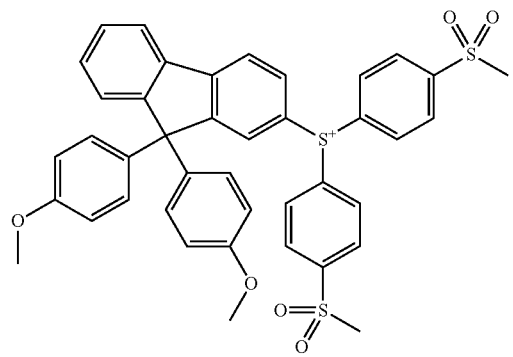
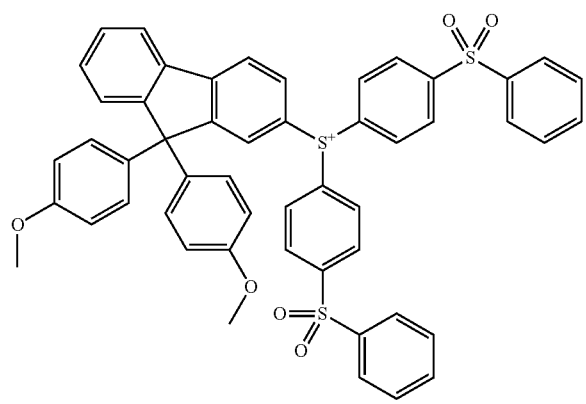
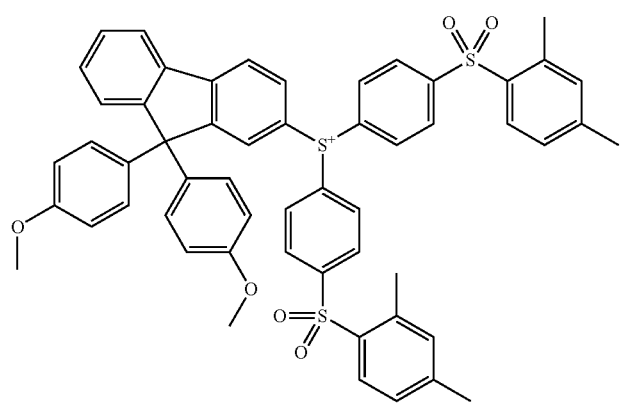

-continued
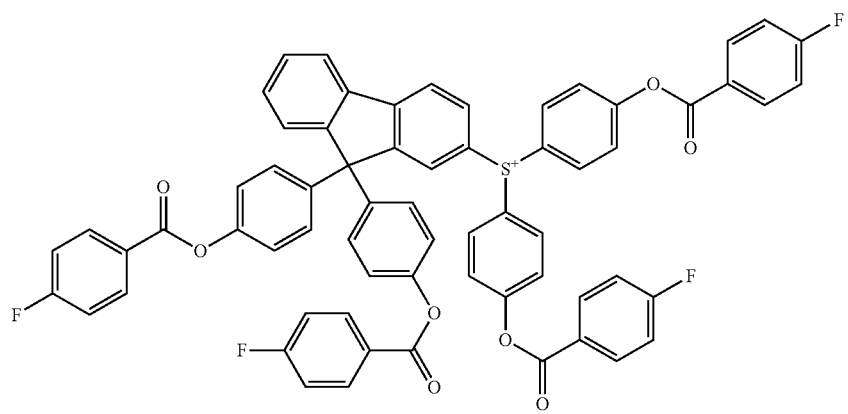
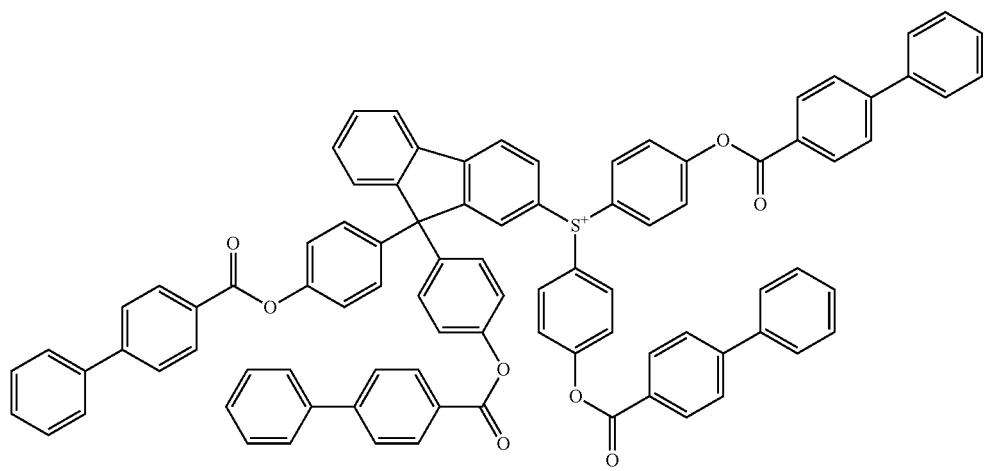
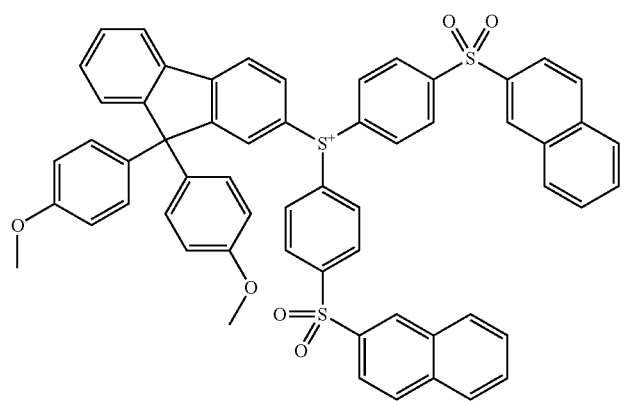
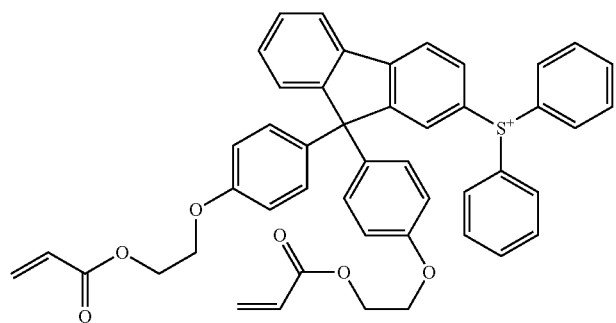

19 20
-continued
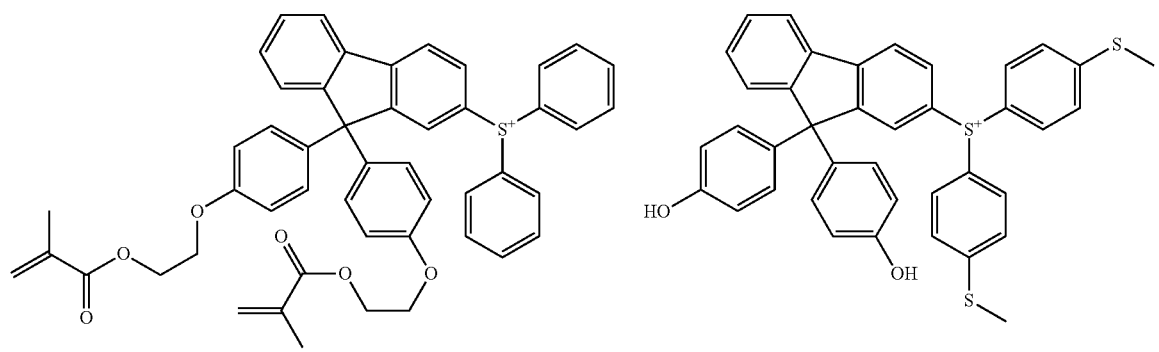
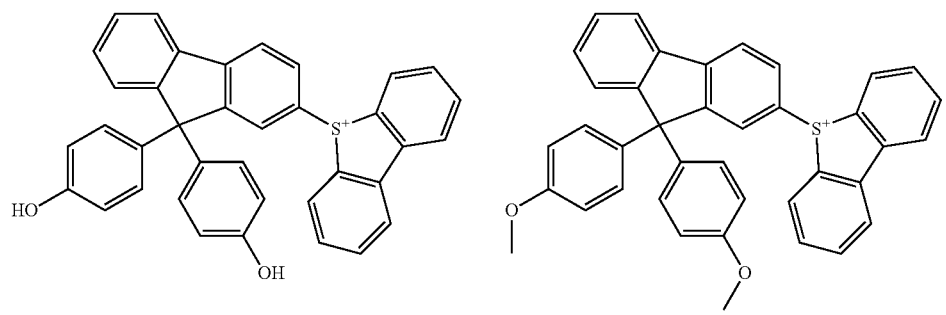
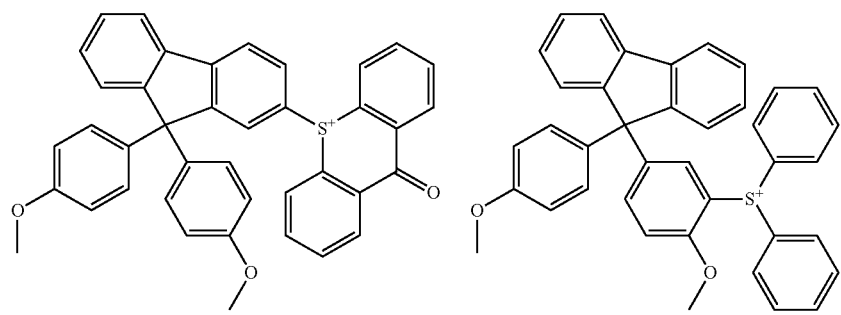
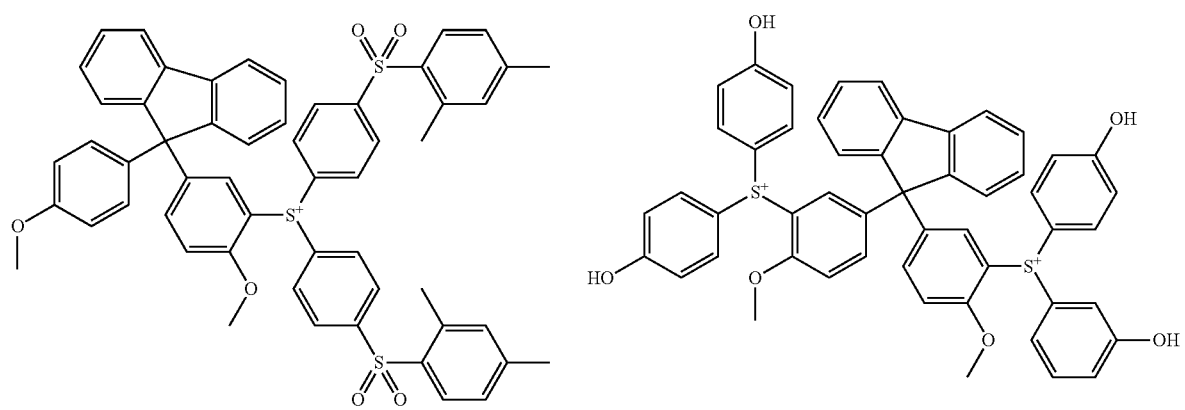

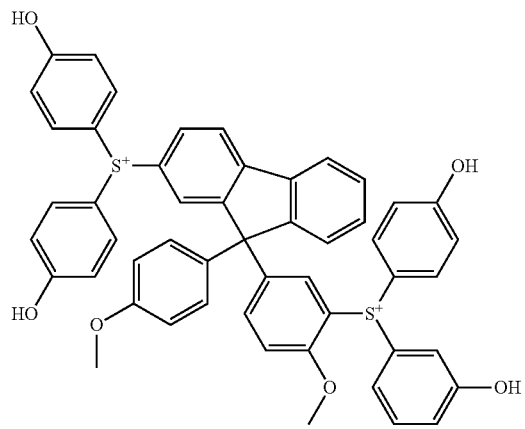

The method for production of the aromatic sulfonium salt compound of the present invention is not limited, and methods applying well-known organic synthesis reactions can be used. For example, it can be obtained by sulfoniation of a diarylsulfoxide compound and a diarylfluorene compound to obtain a sulfonium salt compound, which is then subjected to a salt exchange reaction using as required a salt compound for introduction of an anion component $pAn^{q-}$.

The aromatic sulfonium salt compound of the present invention has a property to release a Lewis acid by irradiation of an active energy line such as a far ultraviolet ray, electron beam, radiation or high frequency wave, including EUV (Extreme Ultra-Violet), X-ray, $F_2$, ArF, KrF, I-ray, H-ray and G-ray, and can act on an acid-reactive organic substance to cause degradation or polymerization thereof. Therefore, the sulfonium salt compound of the present invention is useful as a photoacid generator or as a cationic polymerization initiator for a positive-type and negative-type photoresist.

The amount to be used of the photoacid generator of the present invention comprising the above-described sulfonium salt compound is not limited, and is preferably 0.05 to 100 parts by mass, more preferably 0.05 to 20 parts by mass with respect to 100 parts by mass of the acid-reactive organic substance. Its amount to be blended can also be larger or smaller than the above-mentioned range depending on properties of the acid-reactive organic substance, irradiation intensity of the light, time required for the reaction, physical properties, cost and the like.

The photoacid generator of the present invention is free, as much as possible, from impurity metallic elements other than the components constituting it, impurity halogens such as impurity chlorine, and impurity organic components.

The amount of each impurity metallic element is preferably not more than 100 ppb, more preferably not more than 10 ppb, and the total amount of the impurity metallic elements is preferably not more than 1 ppm, more preferably not more than 100 ppb. The amount of the impurity halogens is preferably not more than 100 ppm, more preferably not more than 10 ppm, still more preferably not more than 1 ppm. The total amount of the impurity organic components is preferably not more than 500 ppm, more preferably not more than 50 ppm, most preferably not more than 10 ppm.

One of the reasons which make the compound of the present invention preferred as a photoacid generator for the above-described photoresist is the fact that the sulfonium salt compound of the present invention is solid and can be purified by recrystallization to a demanded purity.

The resist composition of the present invention is a resist composition containing, together with a resin (hereinafter also referred to as "resist base resin") whose solubility to a developer changes due to the action of an acid, the aromatic sulfonium salt compound of the present invention as an essential photoacid generator.

The resist base resin used for the resist composition of the present invention is not limited, and preferably has a structure which attains low absorption coefficients at wavelengths of active energy lines and a high etching resistance.

Examples of such a resist base resin include polyhydroxystyrene and derivatives thereof; polyacrylic acid and derivatives thereof; polymethacrylic acid and derivatives thereof; copolymers formed from monomers selected from hydroxystyrene, acrylic acid and methacrylic acid and derivatives thereof; copolymers formed from 3 or more types of monomers selected from cycloolefin and derivatives thereof, maleic acid anhydride, and acrylic acid and derivatives thereof; copolymers formed from 3 or more types of monomers selected from cycloolefin and derivatives thereof, maleimide, and acrylic acid and derivatives thereof; and high molecular weight polymers produced by subjecting one or more types of high molecular weight polymers selected from the group consisting of a polynorbornene and a ring-opening metathesis polymer to partial substitution with acid labile groups having an alkali solubility control capability.

Detailed specific examples of the resist base resin are disclosed in, for example, claims 8 to 11 in Japanese Unexamined Patent Application Publication No. 2003-192665 and claim 3 in Japanese Unexamined Patent Application Publication No. 2004-323704.

The weight average molecular weight (Mw) of such a resist base resin based on polystyrene according to gel permeation chromatography (GPC) is usually 3,000 to 300,000, preferably 4,000 to 200,000, more preferably 5,000 to 100,000. With Mw of the base resin lower than 3,000, the heat resistance as a resist tends to decrease, and on the other hand, with Mw thereof higher than 300,000, the developing property as a resist tends to decrease.

As long as the photoacid generator in the resist composition of the present invention contains the aromatic sulfonium salt compound of the present invention as an essential component, another photoacid generator may also be used as an arbitrary component. The amount of the photoacid generator to be used is usually 0.05 to 10 parts by mass, preferably 0.5 to 7 parts by mass with respect to 100 parts by mass of the resist base resin in view of ensuring a sensitivity and a developing property as a resist. With the amount of the photoacid generator to be used less than 0.05 parts by mass, the sensitivity and developing property may decrease, and on the other hand, with the amount thereof more than 10 parts by mass, the transparency for radiation may decrease, leading to difficulty in obtaining a rectangle resist pattern.

When used, the resist composition is normally dissolved in a solvent such that the total solids concentration becomes usually 5 to 50% by weight, preferably 10 to 25% by weight, and adjusted by, for example, filtration through a filter having a hole diameter of about 0.2 μm.

The resist composition of the present invention is useful especially as a chemically-amplified resist. The chemically-amplified resist means a resist wherein acid-dissociable groups in the base resin are dissociated by an action of an acid generated from the photoacid generator by exposure, to yield an acidic functional group, preferably a carboxyl group which, as a result, causes a high solubility of the exposed area of the resist to an alkaline developer, which exposed area is then dissolved and removed by the alkaline developer to produce a positive-type resist pattern.

The light source used for exposure of the resist composition is selected as appropriate from a visible light, ultraviolet ray, far ultraviolet ray, X-ray, charged particle beam and the like depending on the type of photoacid generator employed, and the present invention can be preferably used for resist compositions using various radiations such as far ultraviolet rays including KrF excimer laser (wavelength, 248 nm) and ArF excimer laser (wavelength, 193 nm); X rays including synchrotron radiations; and charged particle beams including electron beams and EUV.

The cationically polymerizable composition of the present invention is a composition containing the cationic polymerization initiator of the present invention comprising the above-described aromatic sulfonium salt compound and a cationically polymerizable compound, and is widely useful in fields of application such as preparation of printing matrices for lithography and letterpress; photoresists for preparation of printed boards, ICs and LSIs; formation of images such as relief images and replicated images; and photo-curing inks, paints and adhesives.

A single type or a mixture of two or more types of the cationically polymerizable compound used for the cationically polymerizable composition of the present invention is used such that a polymer can be obtained by cationic polymerization.

Representative cationically polymerizable compounds are epoxy compounds and oxetane compounds. These are preferred compounds since they are easily available and convenient in terms of handling.

Among these, examples of suitable epoxy compounds include alicyclic epoxy compounds, aromatic epoxy compounds and aliphatic epoxy compounds.

Specific examples of the alicyclic epoxy compounds include polyglycidyl ethers which are polyols having at least one alicyclic ring, and cyclohexene oxide- and cyclopentene oxide-containing compounds obtained by epoxidation of cyclohexene and cyclopentene ring-containing compounds by an oxidizing agent. Examples thereof include hydrogenated bisphenol A diglycidyl ether, 3,4-epoxycyclohexylmethyl-3,4-epoxycyclohexanecarboxylate, 3,4-epoxy-1-methylcyclohexyl-3,4-epoxy-1-methylcyclohexanecarboxylate, 6-methyl-3,4-epoxycyclohexylmethyl-6-methyl-3,4-epoxycyclohexanecarboxylate, 3,4-epoxy-3-methylcyclohexylmethyl-3,4-epoxy-3-methylcyclohexanecarboxylate, 3,4-epoxy-5-methylcyclohexylmethyl-3,4-epoxy-5-methylcyclohexanecarboxylate, 2-(3,4-epoxycyclohexyl-5, 5-spiro-3,4-epoxy)cyclohexane-meta-dioxane, bis(3,4-epoxycyclohexylmethyl)adipate, 3,4-epoxy-6-methylcyclohexylcarboxylate, methylenebis(3,4-epoxycyclohexane), dicyclopentadiene diepoxide, ethylenebis(3,4-epoxycyclohexanecarboxylate), dioctyl epoxyhexahydrophthalate, and di-2-ethylhexyl epoxyhexahydrophthalate.

Examples of commercially available products which may be preferably used as the above-described alicyclic epoxy resins include UVR-6100, UVR-6105, UVR-6110, UVR-6128 and UVR-6200 (all of these are manufactured by Union Carbide Corporation); Celloxide 2021, Celloxide 2021P, Celloxide 2081, Celloxide 2083, Celloxide 2085, Celloxide 2000, Celloxide 3000, Cyclomer A200, Cyclomer M100, Cyclomer M101, Epolead GT-301, Epolead GT-302, Epolead 401, Epolead 403, ETHB and Epolead HD300 (all of these are manufactured by DAICEL CHEMICAL INDUSTRIES, LTD.); and KRM-2110 and KRM-2199 (both of these are manufactured by ADEKA CORPORATION).

Among the above-described alicyclic epoxy resins, those having the cyclohexene oxide structure is preferred in view of curability (curing rate).

Specific examples of the aromatic epoxy resins include polyphenols having at least one aromatic ring, and polyglycidyl ethers of its alkyleneoxide adduct; such as bisphenol A, bisphenol F, and glycidyl ethers and epoxy novolac resins of compounds produced by addition of alkyleneoxide to them.

Specific examples of the aliphatic epoxy resins include aliphatic polyols and polyglycidyl ethers of their alkyleneoxide adducts; polyglycidyl esters of aliphatic long-chain polybasic acids; homopolymers synthesized by vinyl polymerization of glycidyl acrylate or glycidyl methacrylate; and copolymers synthesized by vinyl polymerization of glycidyl acrylate or glycidyl methacrylate and other vinyl monomers. Examples of the representative compounds include glycidyl ethers of polyols such as 1,4-butanediol diglycidyl ether, 1,6-hexanediol diglycidyl ether, triglycidyl ethers of glycerin, triglycidyl ethers of trimethylolpropane, tetraglycidyl ethers of sorbitol, hexaglycidyl ethers of dipentaerythritol, diglycidyl ethers of polyethylene glycol, and diglycidyl ethers of polypropylene glycol; ployglycidyl ethers of polyether polyols obtained by addition of 1 or more types of alkylene oxide to aliphatic polyols such as propylene glycol, trimethylolpropane and glycerin; and diglycidyl esters of aliphatic long-chain dibasic acids. Further, the examples include monoglycidyl ethers of higher fatty alcohols; monoglycidyl ethers of phenol, cresol and butylphenol, and polyether alcohols obtained by addition of alkylene oxide to these; glycidyl esters of higher fatty acids; epoxidized soybean oils; epoxy octyl stearate; epoxy butyl stearate; and epoxidized polybutadienes.

Examples of commercially available products which can be preferably used as the above-described aromatic and aliphatic epoxy resins include EPIKOTE 801 and EPIKOTE 828 (both of these are manufactured by Yuka Shell Epoxy K. K.); PY-306, 0163 and DY-022 (all of these are manufactured by Ciba Specialty Chemicals K.K.); KRM-2720, EP-4100, EP-4000, EP-4080, EP-4900, ED-505 and ED-506 (all of these are manufactured by ADEKA CORPORATION); Epolight M-1230, Epolight EHDG-L, Epolight 40E, Epolight 100E, Epolight 200E, Epolight 400E, Epolight 70P, Epolight 200P, Epolight 400P, Epolight 1500NP, Epolight 1600, Epolight 80MF, Epolight 100MF, Epolight 4000, Epolight 3002 and Epolight FR-1500 (all of these are manufactured by KYOEISHA CHEMICAL Co., LTD.); and Suntohto ST0000, YD-716, YH-300, PG-202, PG-207, YD-172 and YDPN638 (all of these are manufactured by Tohto Kasei Co., Ltd.).

Specific examples of the oxetane compounds include 3-ethyl-3-hydroxymethyloxetane, 3-(meta)allyloxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl] benzene, [1-(3-ethyl-3-oxetanylmethoxy)ethyl]phenylether, isobutoxymethyl(3-ethyl-3-oxetanylmethyl)ether, isobornyloxyethyl(3-ethyl-3-oxetanylmethyl)ether, isobornyl(3-ethyl-3-oxetanylmethyl)ether, 2-ethylhexyl(3-ethyl-3-oxetanylmethyl)ether, ethyldiethyleneglycol(3-ethyl-3-oxetanylmethyl)ether, dicyclopentadiene(3-ethyl-3-oxetanylmethyl)ether, dicyclopentenyloxyethyl(3-ethyl-3-oxetanylmethyl)ether, dicyclopentenyl(3-ethyl-3-oxetanylmethyl)ether, tetrahydrofurfuryl(3-ethyl-3-oxetanylmethyl)ether, tetrabromophenyl(3-ethyl-3-oxetanylmethyl)ether, 2-tetrabromophenoxyethyl(3-ethyl-3-oxetanylmethyl)ether, tribromophenyl(3-ethyl-3-oxetanylmethyl)ether, 2-tribromophenoxyethyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, butoxyethyl(3-ethyl-3-oxetanylmethyl)ether, pentachlorophenyl(3-ethyl-3-oxetanylmethyl)ether, pentabromophenyl(3-ethyl-3-oxetanylmethyl)ether, bornyl(3-ethyl-3-oxetanylmethyl) ether, 3,7-bis(3-oxetanyl)-5-oxa-nonane, 3,3'-(1,3-(2-methylenyl)propanediyl bis(oxymethylene))bis-(3-ethyloxetane), 1,4-bis[(3-ethyl-3-oxetanylmethoxy)methyl] benzene, 1,2-bis[(3-ethyl-3-oxetanylmethoxy)methyl] ethane, 1,3-bis[(3-ethyl-3-oxetanylmethoxy)methyl] propane, ethylene glycol bis(3-ethyl-3-oxetanylmethyl) ether, dicyclopentenyl bis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, tricyclodecanediyldimethylene(3-ethyl-3-oxetanylmethyl)ether, trimethylolpropane tris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol bis(3-ethyl-3-oxetanylmethyl)ether, dipentaerythritol hexakis(3-ethyl-3-oxetanylmethyl)ether, dipentaerythritol pentakis(3-ethyl-3-oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dipentaerythritol pentakis(3-ethyl-3-oxetanylmethyl)ether, ditrimethylolpropane tetrakis(3-ethyl-3-oxetanylmethyl)ether, EO-modified bisphenol A bis(3-ethyl-3-oxetanylmethyl)ether, PO-modified bisphenol A bis (3-ethyl-3-oxetanylmethyl)ether, EO-modified hydrogenated bisphenol A bis(3-ethyl-3-oxetanylmethyl) ether, PO-modified hydrogenated bisphenol A bis(3-ethyl-3-oxetanylmethyl)ether, and EO-modified bisphenol F(3-ethyl-3-oxetanylmethyl)ether.

These oxetane compounds are effective especially in cases where flexibility is required, which is preferred.

Specific examples of other compounds for the cationically polymerizable compound include well-known compounds including oxolane compounds such as tetrahydrofuran and 2,3-dimethyltetrahydrofurane; cyclic acetal compounds such as trioxane, 1,3-dioxolan and 1,3,6-trioxanecyclooctane; cyclic lactone compounds such as β-propiolactone and ε-caprolactone; thiirane compounds such as ethylene sulfide and thioepichlorohydrin; thietane compounds such as 1,3-propine sulfide and 3,3-dimethylthietane; cyclic thioether compounds such as tetrahydrothiophene derivatives; vinyl ether compounds such as ethylene glycol divinyl ether, alkyl vinyl ether, 2-chloroethyl vinyl ether, 2-hydroxyethyl vinyl ether, triethylene glycol divinyl ether, 1,4-cyclohexanedimethanol divinyl ether, hydroxybutyl vinyl ether, and the propenyl ether of propylene glycol; spiro ortho ester compounds obtained by the reaction of an epoxy compound and lactone; ethylenically unsaturated compounds such as styrene, vinylcyclohexene, isobutylene and polybutadiene; and silicones.

The amount to be used of the cationic polymerization initiator comprising the aromatic sulfonium salt compound of the present invention is preferably 0.01 part by mass to 10 parts by mass, more preferably 0.1 part by mass to 5 parts by mass with respect to 100 parts by mass of the above-described cationically polymerizable compound. In cases where this amount to be used is smaller than 0.01 part by mass, curing may be insufficient, and on the other hand, in cases where the amount is larger than 10 parts by mass, not only the effect of its usage cannot be increased, but also it may adversely affect the physical property of the cured material.

The cationic polymerization initiator comprising the aromatic sulfonium salt compound of the present invention may be used for the cationically polymerizable composition to which various additives, together with the above-described cationically polymerizable compound, are also blended. Examples of the various additives include organic solvents, benzotriazole, triazine and benzoate ultraviolet absorbers; phenol, phosphorous and sulfur antioxidants; antistatic agents containing cationic surfactants, anionic surfactants, nonionic surfactants or amphoteric surfactants; flame retardants such as halogen compounds, phosphate ester compounds, amide phosphate compounds, melamine compounds, fluorocarbon resins or metal oxides, (poly)melamine phosphate and (poly)piperazine phosphate; hydrocarbon, fatty acid, aliphatic alcohol, aliphatic ester, aliphatic amide and metal soap lubricants; coloring agents such as dyes, pigments and carbon black; inorganic silica additives such as fumed silica, microparticulate silica, silica stone, diatomaceous earths, clay, kaolin, diatomaceous earth, silica gel, calcium silicate, sericite, kaolinite, flint, feldspar powder, vermiculite, attapulgite, talc, mica, minnesotaite, pyrophyllite and silica; fillers such as glass fibers and calcium carbonate; crystallizing agents such as nucleating agents and crystallization promoters; and silane coupling agents.

Examples of uses of the cationic polymerization initiator of the present invention include inks, over-coats (protective layers), paints, adhesives, insulation materials, structural materials, optical three-dimensional moldings, optical films, color filters, FRPs and semiconductor resists.

EXAMPLES

The present invention will be described more concretely by way of Examples and Comparative Examples, but the present invention is not limited to these Examples and the like.

Examples 1 to 12 below describe production examples of the aromatic sulfonium salt compounds No. 1 to No. 12. Examples 13 to 17 and Comparative Examples 1 to 3 below describe evaluation examples by measurement of acid generation efficiencies using respective aromatic sulfonium salts and comparative compounds obtained in Examples 1 to 4 and 12. Example 18 and Comparative Examples 4 to 6 below describe evaluation examples of the developing properties with alkali using resist compositions obtained using the aromatic sulfonium salts No. 1 and No. 12 obtained in Examples 1 and 12 and comparative compounds. Example 19 below describes production of a cationically polymerizable composition using the aromatic sulfonium salt No. 1 obtained in Example 1, and evaluation of the curability thereof.

Example 1

Synthesis of trifluoromethanesulfonate[9,9-bis(4-hydroxyphenyl)-9H-fluorene-2-yl]bis(4-hydroxyphenyl)sulfonium (compound No. 1)

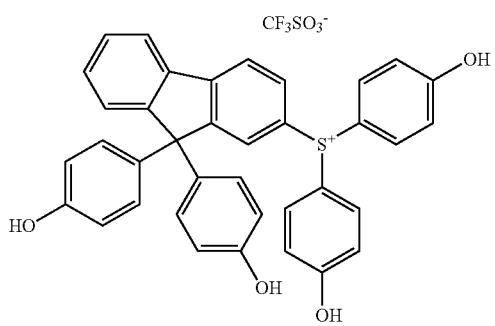

Compound No. 1

To a 3 L three-necked flask, 1441 g (15 moles) of methanesulfonate and 141.9 g (1 mole) of phosphorus pentoxide were fed, and the atmosphere was replaced with nitrogen, followed by heating the mixture at 100° C. to dissolve it. After cooling thereof, 234 g (1 mole) of bis(hydroxyphenyl)sulfoxide and 350 g (1 mole) of 9,9-bis(4-hydroxyphenyl)-9H-fluorene were added thereto, and the resulting mixture was allowed to react at 15° C. for 2 hours. Subsequently, 5000 g of ice water and 2500 g of methanol were mixed with each other and the above reaction solution was added to this mixture. Precipitated solids were collected by filtration, and 4000 g of methyl isobutyl ketone and 3000 g of water were added thereto, followed by stirring the resulting mixture. To this mixture, 158 g (1.01 moles) lithium trifluoromethanesulfonate was added, and the resulting mixture was stirred for 2 hours. The methyl isobutyl ketone layer was washed 3 times with 3000 g of water and concentrated under reduced pressure to obtain 587 g of white solids. These were subjected to a silica gel chromatography and fractions containing the desired product were recovered, followed by concentration thereof under reduced pressure to obtain white solids. To these, 2000 g of water and 2000 g of methanol were added, and the resulting mixture was heated and dissolved, followed by cooling the solution slowly to allow colorless crystals to precipitate slowly. The precipitated crystals were filtered. These manipulations were repeated 3 times and the resulting crystals were dried to obtain the compound No. 1. The yielded amount was 164 g and the yield was 23%.

Example 2

Synthesis of trifluoromethanesulfonate[9,9-bis(4-methoxyphenyl)-9H-fluorene-2-yl]bis(4-methoxyphenyl)sulfonium (compound No. 2)

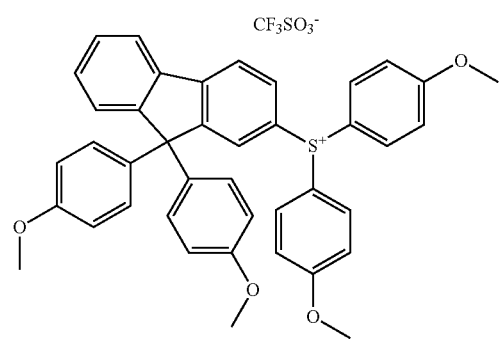

Compound No. 2

In a 100 mL four-necked flask, 7.17 g (0.01 mole) of trifluoromethanesulfonate[9,9-bis(4-hydroxyphenyl)-9H-fluorene-2-yl]bis(4-hydroxyphenyl)sulfonium obtained in Example 1 and 22 g of dimethylformamide were placed and allowed to dissolve, followed by addition of 11.06 g (0.08 mole) of potassium carbonate to the resulting solution, stirring of the resulting mixture and replacement of the atmosphere by nitrogen. To the mixture, 6.39 g (0.045 mole) of methyl iodide was added dropwise, and the resulting mixture was allowed to react by stirring at room temperature for 8 hours. To the reaction solution, 100 mL of methylene chloride was fed and allowed to dissolve thereinto, followed by washing 3 times with 100 mL of water. The organic layer was dried over sodium sulfate and the solvent was evaporated to obtain a crude product, which was then subjected to a silica gel chromatography to obtain the compound No. 2. The yielded amount was 4.25 g and the yield was 55%.

Example 3

Synthesis of trifluoromethanesulfonate[9,9-bis(4-t-butoxycarbonyloxyphenyl)-9H-fluorene-2-yl]bis(4-t-butoxycarbonyloxyphenyl)sulfonium (compound No. 3)

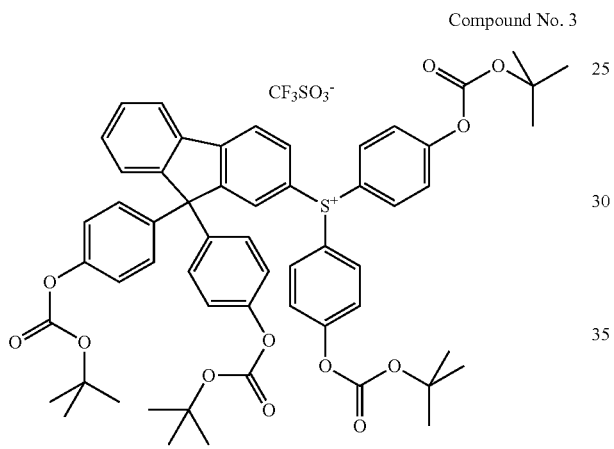

Compound No. 3

To a 100 mL four-necked flask, 7.17 g (0.01 mole) of trifluoromethanesulfonate[9,9-bis(4-hydroxyphenyl)-9H-fluorene-2-yl]bis(4-hydroxyphenyl)sulfonium obtained in Example 1, 25 g of pyridine, 0.32 g (0.001 mole) of tetrabutylammonium bromide and 8.73 g (0.04 mole) of di-tert-butyl dicarbonate were fed, and the atmosphere was replaced with nitrogen, followed by allowing the resulting mixture to react by stirring at 60° C. for 48 hours. To the reaction solution, 300 g of dichloroethane was added and it was allowed to dissolve, followed by washing the resulting solution with 500 g of water and evaporating the solvent by distillation under reduced pressure to obtain solids. These solids were allowed to dissolve into 500 g of methanol at 50° C., and water was added to the resulting solution, thereby allowing the resulting mixture to yield white precipitates. These precipitates were filtered and washed by repeating reprecipitation with methanol and water 2 times, followed by drying the resultant to obtain the compound No. 3. The yielded amount was 5.70 g and the yield was 51%.

Example 4

Synthesis of nonafluorobutanesulfonate[9,9-bis(4-hydroxyphenyl)-9H-fluorene-2-yl]bis(4-hydroxyphenyl)sulfonium (compound No. 4)

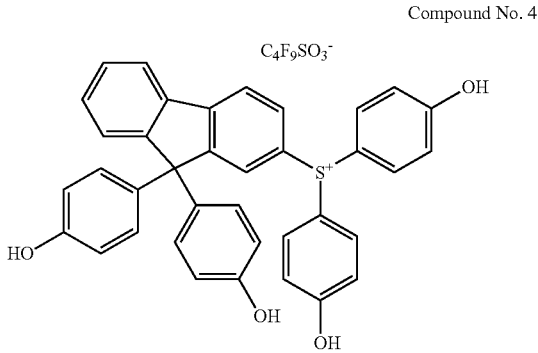

Compound No. 4

By following the same procedure as in Example 1 except that potassium nonafluorobutanesulfonate was used instead of lithium trifluoromethanesulfonate, the compound No. 4 was obtained as white powder. The yielded amount was 182 g, and the yield was 21%.

Example 5

Synthesis of trifluoromethanesulfonate[9,9-bis(4-methoxyphenyl)-9H-fluorene-2-yl]bis(4-benzenesulfonylphenyl)sulfonium (compound No. 5)

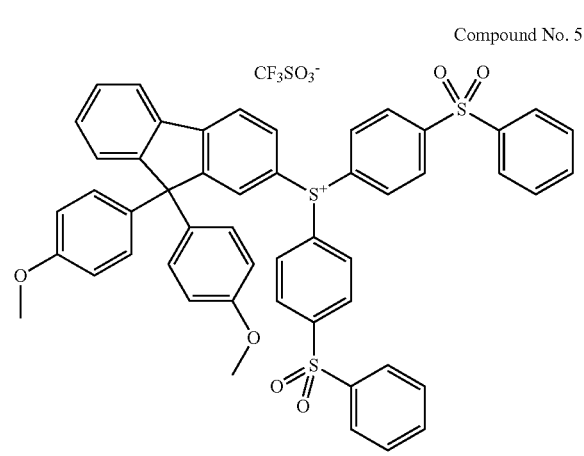

Compound No. 5

To a 100 mL four-necked flask, 360 g (3.75 moles) of methanesulfonate and 35.5 g (0.25 mole) of phosphorus pentoxide were fed, and the atmosphere was replaced with nitrogen, followed by heating the mixture at 100° C. to dissolve it.

After cooling thereof, 59.6 g (0.25 mole) of bis(4-fluorophenyl)sulfoxide and 87.5 g (0.25 mole) of 9,9-bis(4-hydroxyphenyl)-9H-fluorene were fed to the solution, and the resulting mixture was allowed to react by stirring at 50° C. for 2 hours. Subsequently, 2000 mL of ice water and 1000 mL of methanol were mixed with each other and the above reaction solution was added to this mixture. To this, 1000 mL of methylene chloride, 500 mL of water and 40.6 g (0.26 mole) of lithium trifluoromethanesulfonate were added, and the resulting mixture was stirred for 2 hours. The methylene chloride layer was washed 3 times with 500 mL of water and concentrated under reduced pressure to obtain white solids, which was then subjected to a silica gel chromatography. Fractions containing the desired products were collected and concentrated under reduced pressure to obtain 54.1 g of trifluoromethanesulfonate [9,9-bis(4-hydroxyphenyl)-9H-fluorene-2-yl]bis(4-fluorophenyl)sulfonium. The yield was 30%. In a 50 mL four-necked flask, 5.41 g of this crude product was allowed to dissolve into 10.8 g of dimethylformamide, and 0.84 g (0.021 mole) of sodium hydroxide and 0.061 g ($1.5 \times 10^{-4}$ mole) of tetrabutylammonium hydrosulfate were added to the resulting solution, followed by addition of 2.09 g (0.019 mole) of benzene thiol thereto dropwise and stirring of the resulting mixture for 3 hours. To this mixture, 55 mL of methylene chloride was fed, and the resulting mixture was washed 3 times with 50 mL of water, followed by concentrating the resultant under reduced pressure to obtain 6.89 g of a crude product. To a 50 mL four-necked flask, this crude product and 50.0 g of dichloroethane were fed, and the crude product was allowed to dissolve into dichloroethane, followed by addition of 20.0 g of ethanol and 0.125 g ($3.8 \times 10^{-4}$ mole) of sodium tungstate dihydrate to the resulting solution and stirring thereof. To this, 6.80 g (0.060 mole) of 30% aqueous hydrogen peroxide solution was added dropwise, and the resulting mixture was heated to 50° C. and stirred for 3 hours. To the resultant, 50 mL of dichloroethane was fed, and the resulting mixture was washed 3 times with 50 mL of water, followed by concentrating the mixture under reduced pressure to obtain 6.37 g of a crude product. To a 50 mL four-necked flask, this crude product and 40 mL of dimethylformamide were fed, and the crude product was allowed to dissolve into dimethylformamide, followed by addition of 4.20 g (0.030 mole) of potassium carbonate to the resulting solution. To the resulting mixture, 2.06 g (0.015 mole) of methyl iodide was added dropwise, and the mixture was stirred for 3 hours. To this mixture, 40 mL of methylene chloride was fed, and the resulting mixture was washed 3 times with 40 mL of water, followed by concentrating the resultant under reduced pressure to obtain a crude product. The MALDI-TOFMASS of the crude product was measured to find a peak at 1308.32, so that coexistence of single fluorene bisphenol molecules wherein sulfoniation occurred at 2 positions (compound No. 5B) was confirmed. The crude product was subjected to a silica gel chromatography and fractions containing the desired product were collected, followed by concentrating thereof under reduced pressure to obtain the compound No. 5. The yielded amount was 3.41 g and the yield was 46%.

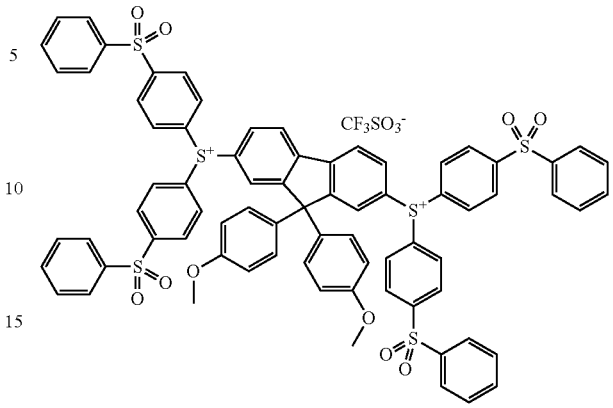

Compound No. 5B

Example 6

Synthesis of trifluoromethanesulfonate[9,9-bis(4-methoxyphenyl)-9H-fluorene-2-yl]bis(4-butanesulfonylphenyl)sulfonium (compound No. 6)

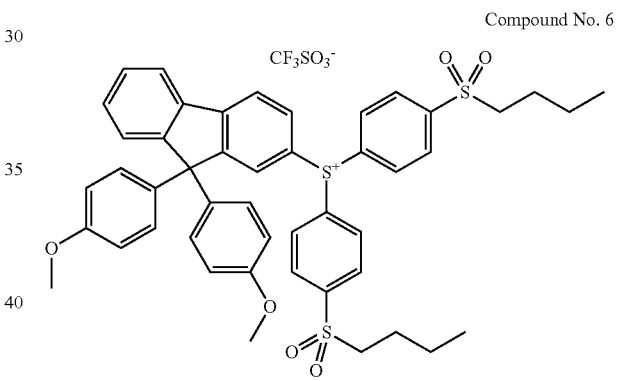

Compound No. 6

To 25 g of dimethylformamide, 5.41 g of trifluoromethaesulfonate[9,9-bis(4-hydroxyphenyl)-9H-fluorene-2-yl]bis(4-fluorophenyl)sulfonium synthesized by the method described in Example 5 was dissolved, and 0.84 g (0.021 mole) of sodium hydroxide and 0.061 g ($1.5 \times 10^{-4}$ mole) of tetrabutylammonium hydrosulfate were added to the resulting solution, followed by addition of 1.71 g (0.019 mole) of 1-butane thiol thereto dropwise and stirring of the resulting mixture for 3 hours. To this mixture, 50 mL of methylene chloride was fed, and the resulting mixture was washed 3 times with 50 mL of water, followed by concentrating the resultant under reduced pressure to obtain 6.66 g of a crude product. To a 50 mL four-necked flask, this crude product and 30.0 g of dichloroethane were fed, and the crude product was allowed to dissolve into dichloroethane, followed by addition of 12.0 g of ethanol and 0.125 g ($3.8 \times 10^{-4}$ mole) of sodium tungstate dihydrate to the resulting solution and stirring thereof. To this, 6.80 g (0.060 mole) of 30% aqueous hydrogen peroxide solution was added dropwise, and the resulting mixture was heated to 50° C. and stirred for 3 hours. To the resultant, 50 mL of dichloroethane was fed, and the resulting mixture was washed 3 times with 50 mL of water, followed by concentrating the mixture under reduced pressure to obtain 5.69 g of a crude product. To a 50 mL four-necked flask, this crude product and 30 mL of dimethylformamide were fed, and the crude product was allowed to dissolve into dimethylformamide, followed by addition of 3.91 g (0.028 mole) of potassium carbonate to the resulting solution. To the resulting mixture, 1.92 g (0.014 mole) of methyl iodide was added dropwise, and the mixture was stirred for 3 hours. To this mixture, 50 mL of methylene chloride was fed, and the resulting mixture was washed 3 times with 50 mL of water, followed by concentrating the resultant under reduced pressure to obtain a crude product. This was subjected to a silica gel chromatography and fractions containing the desired product were collected, followed by concentrating thereof under reduced pressure to obtain the compound No. 6. The yielded amount was 3.11 g and the yield was 42%.

Example 7

Synthesis of trifluoromethanesulfonate[9,9-bis(4-methanesulfonyloxyphenyl)-9H-fluorene-2-yl]bis(4-methanesulfonyloxyphenyl)sulfonium (compound No. 7)

Compound No. 7

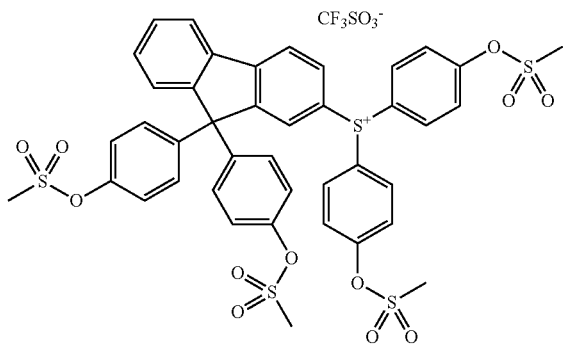

To a 100 mL four-necked flask, 7.17 g (0.01 mole) of the compound No. 1 obtained in Example 1 and 40 g of dimethylformamide were fed, and the compound No. 1 was allowed to dissolve into dimethylformamide, followed by addition of 4.25 g (0.042 mole) of triethylamine thereto, stirring of the resulting mixture and replacement of the atmosphere with nitrogen. To this mixture, 4.81 g (0.042 mole) of methanesulfonyl chloride was added dropwise, and the resulting mixture was stirred at room temperature for 1 hour to allow the reaction to proceed. To this reaction solution, 60 mL of methylene chloride was fed and it was allowed to dissolve thereinto, followed by washing the resulting solution 3 times with 60 mL of water. The solution was then concentrated under reduced pressure to obtain a crude product, which was then subjected to a silica gel chromatography and concentrated under reduced pressure to obtain the compound No. 7. The yielded amount was 4.25 g and the yield was 55%.

Example 8

Synthesis of trifluoromethanesulfonate[9,9-bis(4-hydroxyphenyl)-9H-fluorene-2-yl]bis(4-acetylphenyl)sulfonium (compound No. 8)

Compound No. 8

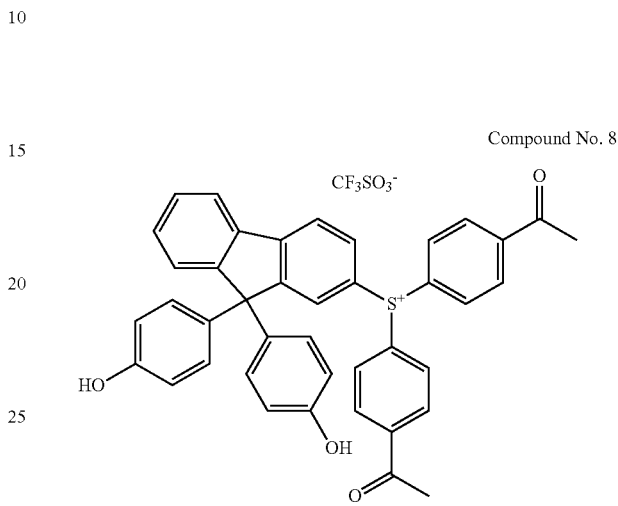

To a 300 mL four-necked flask, 20.0 g (0.107 mole) of diphenyl sulfide and 140.0 g of chlorobenzene were fed, and the resulting mixture was stirred and allowed to dissolve. To the resulting solution, 31.5 g (0.236 mole) of aluminum chloride was added, and the resulting mixture was cooled to 10° C., followed by addition of 17.7 g (0.225 mole) of acetyl chloride dropwise thereto while keeping a temperature of not more than 20° C., and allowing the resulting mixture to react by stirring thereof at 10° C. for 2 hours. The reaction solution was added to a mixture of 1000 g of ice water and 1000 mL of methylene chloride with stirring at a temperature of not more than 30° C. The methylene chloride layer was washed 3 times with 1000 mL of water and concentrated under reduced pressure, followed by addition of 1000 mL of methanol to the resultant, collection of the yielded crystals by filtration and drying thereof to obtain 19.67 g of bis(4-acetylphenyl)sulfide. The yield was 68%. To a 100 mL four-necked flask, 6.22 g (0.023 mole) of bis(4-acetylphenyl)sulfide, 60.0 g of acetic acid and 40 g of dichloroethane were fed, and the resulting mixture was allowed to dissolve under heat. To the resulting solution, 0.18 g (0.001 mole) of 20% aqueous solution of titanium trichloride was added, and 2.07 g (0.018 mole) of 30% aqueous hydrogen peroxide solution was added thereto dropwise, followed by stirring the resulting mixture for 2 hours. To this mixture, 100 mL of water was added, and the resulting mixture was cooled to 10° C., followed by collection of yielded crystals by filtration. These crystals were washed with 30 mL of methanol and collected by filtration, followed by drying thereof to obtain 6.39 g of bis(4-acetylphenyl) sulfoxide. The yield was 97%. By following the same procedure as in Example 1 except that 5.73 g (0.020 mole) of bis(4-acetylphenyl)sulfoxide was used instead of bis(hydroxyphenyl)sulfoxide, the compound No. 8 was obtained. The yielded amount was 3.98 g, and the yield was 26%.

Example 9

Synthesis of trifluoromethanesulfonate-5-[9,9-bis(4-hydroxyphenyl)-9H-fluorene-2-yl]dibenzothiophenium (compound No. 9)

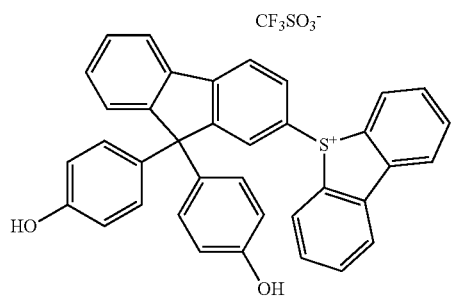

Compound No. 9

By following the same procedure as in Example 1 except that 8.01 g (0.04 mole) of dibenzothiophene-5-oxide was used instead of bis(hydroxyphenyl)sulfoxide, the compound No. 9 was obtained as pale yellow powder. The yielded amount was 8.15 g, and the yield was 30%.

Example 10

Synthesis of trifluoromethanesulfonate[9,9-bis[4-(4-fluorobenzoyloxy)phenyl]-9H-fluorene-2-yl]bis[4-(4-fluorobenzoyloxy)phenyl]sulfonium (compound No. 10)

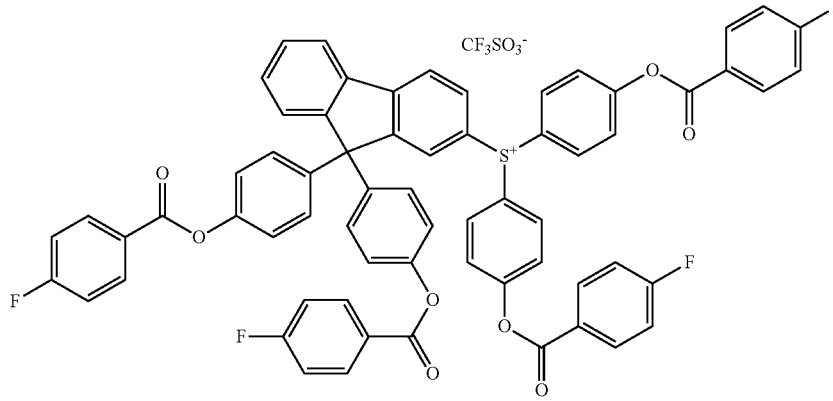

Compound No. 10

To a 100 mL four-necked flask, 7.17 g (0.01 mole) of trifluoromethanesulfonate[9,9-bis(4-hydroxyphenyl)-9H-fluorene-2-yl]bis(4-hydroxyphenyl)sulfonium obtained in Example 1 and 70 g of dimethylformamide were fed, and the resulting mixture was allowed to dissolve, followed by addition of 7.08 g (0.07 mole) of triethylamine to the resulting solution. After replacement of the atmosphere with nitrogen, the mixture was cooled to 5° C., and 9.51 mole (0.06 mole) of 4-fluorobenzoyl chloride was added dropwise thereto while keeping a liquid temperature of not more than 10° C., followed by stirring the resulting mixture at 25° C. for 4 hours. The mixture was sufficiently cooled and 70 mL of methylene chloride was added thereto, followed by washing the resulting mixture 3 times with 70 mL of water and concentrating thereof under reduced pressure to obtain a crude product. The obtained crude product was dissolved into 70 mL of methylene chloride again, and the resulting solution was added to 250 mL of isopropyl ether, followed by stirring of the resulting mixture for 1 hour and collecting yielded solids by filtration, which solids were then subjected to a silica gel chromatography. Reprecipitation was carried out with methylene chloride-isopropyl ether again, and yielded solids were recovered and dried to obtain the compound No. 10. The yielded amount was 4.80 g, and the yield was 40%.

Example 11

Synthesis of trifluoromethanesulfonate bis[4-(2,4-dimethylbenzenesulfonyl)phenyl][2-methoxy-[5-(9H-fluorene-9-yl(4-methoxyphenyl)methyl)phenyl] sulfonium (compound No. 11)

Compound No. 11

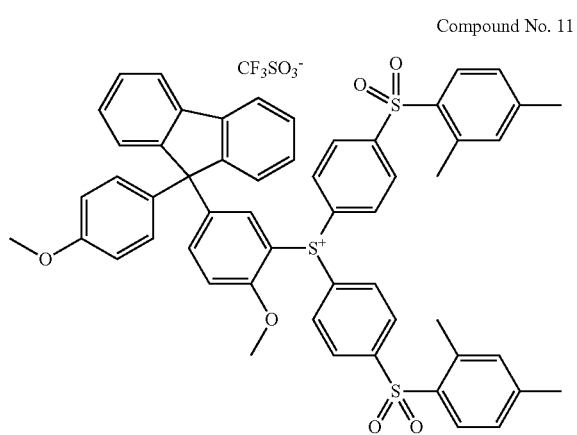

To a 500 mL four-necked flask, 35.0 g (0.10 mole) of 9,9-bis(4-hydroxyphenyl)-9H-fluorene and 300 mL of dimethylformamide were fed, and the resulting mixture was allowed to dissolve, followed by addition of 63.6 g (0.46 mole) of potassium carbonate to the resulting solution. The resulting mixture was cooled to 10° C. and 31.2 g (0.22 mole) of methyl iodide was added thereto dropwise, followed by stirring the mixture for 6 hours. To this mixture, 500 mL of methyl isobutyl ketone was fed, and the resulting mixture was washed 3 times with 400 mL of water, followed by concentrating thereof under reduced pressure to obtain a crude product. To this crude product, 300 mL of methyl isobutyl ketone was added and the crude product was allowed to dissolve under heat, followed by addition of 300 mL of methanol, collection of yielded crystals by filtration and drying thereof to obtain 29.7 g of 9,9-bis(4-methoxyphenyl)-9H-fluorene. The yield was 79%. On the other hand, 4.77 g (0.02 mole) of bis(4-fluorophenyl)sulfoxide and 30 ml of dimethylformamide were fed to a 100 mL four-necked flask and allowed to dissolve, followed by addition of 2.20 g (0.055 mole) of sodium hydroxide and 1.60 g ($4.0 \times 10^{-3}$ mole) of tetrabutylammonium hydrosulfate to the resulting solution and replacement of the atmosphere with nitrogen. To this mixture, 6.91 g (0.05 mole) of 2,4-dimethylbenzenethiol was added dropwise, and the resulting mixture was heated to 48° C. and stirred for 11 hours. To this mixture, 500 mL of ethyl acetate was fed, and the resulting mixture was washed 4 times with 300 mL of water and concentrated under reduced pressure to yield crystals which were then collected by filtration and dried to obtain 5.67 g of bis[4-(2,4-dimethylphenylsulfanyl)phenyl]sulfoxide. The yield was 60%. By following the same procedure as in Example 1 except that 2.28 g (0.0048 mole) of bis[4-(2,4-dimethylphenylsulfanyl)phenyl]sulfoxide was used instead of bis(hydroxyphenyl)sulfoxide and that 1.75 g (0.0048 mole) of 9,9-bis(4-methoxyphenyl)-9H-fluorene was used instead of 9,9-bis(4-hydroxyphenyl)-9H-fluorene, 3.48 g of trifluoromethanesulfonate bis[4-(2,4-dimethylbenzenesulfanyl)phenyl][2-methoxy-[5-(9H-fluorene-9-yl(4-methoxyphenyl)methyl)phenyl]sulfonium was obtained. The yield was 74%. To a 50 mL four-necked flask, 0.99 g ($1.0 \times 10^{-3}$ mole) of the obtained compound and 10.0 g of acetic acid were fed and the compound was allowed to dissolve, followed by addition of 0.0165 g ($5.0 \times 10^{-5}$ mole) of sodium tungstate dihydrate and dropwise addition of 0.91 g ($8.0 \times 10^{-3}$ mole) of 30% aqueous hydrogen peroxide solution to the resulting solution, heating of the resulting mixture to 60° C. and stirring thereof for 3 hours. To the mixture, 30 mL of methyl isobutyl ketone was fed, and the resulting mixture was washed 3 times with 30 mL of water, followed by concentrating thereof under reduced pressure. The MALDI-TOFMASS of this crude product was measured to find a peak at 1307.22, so that coexistence of single fluorene bisphenol molecule wherein sulfoniation occurred at 2 positions (compound No. 11B) was confirmed. This product was dissolved into 30 mL of methyl isobutyl ketone again and 30 mL of p-xylene was added to the resulting solution, followed by collection of yielded crystals by filtration and drying thereof to obtain the compound No. 11. The yielded amount was 0.051 g, and the yield was 4.8%.

Compound No. 11B

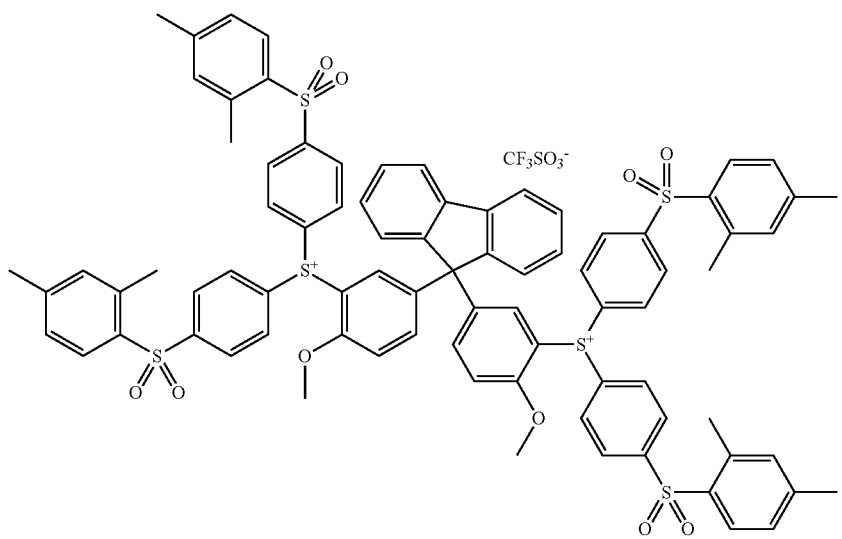

Example 12

Synthesis of trifluoromethanesulfonate[2-methoxy-[5-(9H-fluorene-9-yl(4-methoxyphenyl)methyl)phenyl]diphenylsulfonium (compound No. 12)

Compound No. 12

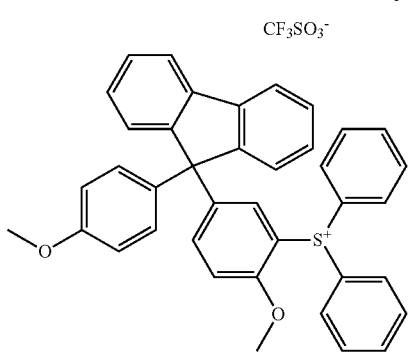

By following the same procedure as in Example 1 except that 4.04 g (0.02 mole) of diphenylsulfoxide was used instead of bis(hydroxyphenyl)sulfoxide and that 7.31 g (0.02 mole) of 9,9-bis(4-methoxyphenyl)-9H-fluorene obtained in Example 11 was used instead of 9,9-bis(4-hydroxyphenyl)-9H-fluorene, the compound No. 12 was obtained. The yielded amount was 8.48 g, and the yield was 60%.

The purities and properties of the compounds 1 to 12 obtained as described above are shown in Table 1, and results of their identification are shown in Table 2. The position of attachment of each compound was determined by various measurements, that is, cosy, HMQC and HMBC NMR using solvents shown in Table 2.

TABLE 1

| | Purity/% (HPLC) | Property | MALDI-TOFMASS(m/z) Upper row: cation mass (theoretical value) Lower row: anion mass (theoretical value) |
|---|---|---|---|
| Compound No. 1 | 99.0 | colorless crystal | 567.02(567) 149.95(149) |
| Compound No. 2 | 99.1 | colorless crystal | 624.77(623) 149.86(149) |
| Compound No. 3 | 99.2 | colorless crystal | 968.09(967) 149.75(149) |
| Compound No. 4 | 99.2 | colorless crystal | 567.81(567) 300.34(299) |
| Compound No. 5 | 98.9 | colorless crystal | 843.37(843) 149.23(149) |
| Compound No. 6 | 95.5 | colorless crystal | 803.56(803) 149.36(149) |
| Compound No. 7 | 97.3 | colorless crystal | 879.43(879) 149.33(149) |
| Compound No. 8 | 97.1 | pale yellow crystal | 620.30(619) 149.21(149) |
| Compound No. 9 | 99.0 | pale yellow crystal | 534.34(533) 149.35(149) |
| Compound No. 10 | 90.1 | yellow crystal | 1071.52(1071) 149.29(149) |
| Compound No. 11 | 98.5 | colorless crystal | 899.65(899) 149.01(149) |
| Compound No. 12 | 96.0 | colorless crystal | 563.23(563) 149.33(149) |

*HPLC measurement condition
Column: "Inertsil ODS-2" 5 μm, 4.6 × 250 mm, 40° C.
Eluent: acetonitrile/water = 9/1 (4.38 g sodium 1-octanesulfonate/1 L water), 1.00 mL/min.
Detector: UV 230 nm

TABLE 2

| | Upper row: 1H NMR Lower row: 19F NMR |
|---|---|
| Compound No. 1 (CDCl$_3$) | 9.43 (s, 4H), 8.21 (d, 1H), 8.01 (d, 1H), 7.77 (s, 1H), 7.61 (d, 4H), 7.44-7.39 (m, 4H), 7.07 (d, 4H), 6.85 (d, 4H), 6.61 (d, 4H) −74.0 (s, 3F) |
| Compound No. 2 | 8.01 (d, 1H), 7.87 (d, 1H), 7.80 (s, 1H), 7.50 (d, 4H), 7.30-7.00 (m, 4H), 6.95 (d, 4H), 6.87 (d, 4H), 6.55 (d, 4H), |

TABLE 2-continued

| | Upper row: 1H NMR<br>Lower row: 19F NMR |
|---|---|
| (CDCl$_3$) | 3.83 (s, 12H)<br>−75.32 (s, 3F) |
| Compound No. 3<br>(CDCl$_3$) | 8.01 (d, 1H), 7.87 (d, 1H), 7.80 (s, 1H), 7.55 (d, 4H),<br>7.50-6.80 (m, 16H), 1.38 (s, 36H)<br>−75.41 (s, 3F) |
| Compound No. 4<br>(CDCl$_3$) | 9.43 (s, 4H), 8.21 (d, 1H), 8.01 (d, 1H), 7.77 (s, 1H),<br>7.61 (d, 4H), 7.44-7.39 (m, 4H), 7.13 (d, 4H), 6.95 (d, 4H),<br>6.61 (d, 4H)<br>−78.0 (s, 3F), −111.8 (s, 2F), −118.8 (s, 2F), 123.2 (s, 2F) |
| Compound No. 5 | 8.03 (d, 4H), 7.87-7.81 (m, 10H), 7.71 (t, 2H), 7.50 (m, 5H),<br>7.43-7.40 (m, 6H), 7.32 (t, 1H), 7.12 (m, 5H), 3.83 (s, 6H) |

TABLE 2-continued

| | Upper row: 1H NMR<br>Lower row: 19F NMR |
|---|---|
| (CDCl$_3$) | −77.45 (s, 3F) |
| Compound No. 6<br>(CDCl$_3$) | 7.86-7.87 (m, 6H), 7.53-7.50 (m, 6H), 7.44 (s, 1H), 7.42<br>(s, 1H), 7.28 (s, 1H), 7.12 (d, 4H), 6.87 (d, 4H), 3.83 (s, 6H),<br>3.13 (t, 4H), 1.61 (m, 4H), 1.31 (m, 4H), 0.90 (t, 6H)<br>−77.23 (s, 3F) |
| Compound No. 7<br>(CDCl$_3$) | 7.89 (d, 1H), 7.87 (d, 1H), 7.53 (d, 1H), 7.50 (s, 1H),<br>7.45-7.40 (m, 6H), 7.33-7.28 (m, 13H), 3.53 (s, 6H),<br>3.51 (s, 6H)<br>−76.94 (s, 3F) |
| Compound No. 8<br>(CDCl$_3$) | 9.43 (s, 2H), 7.94 (d, 4H), 7.87 (d, 1H), 7.85 (d, 1H), 7.54<br>(s, 1H), 7.51 (d, 1H), 7.42 (d, 1H), 7.38 (m, 5H), 7.27 (t, 1H),<br>7.06 (d, 4H), 6.63 (d, 4H), 2.50 (s, 6H)<br>−77.48 (s, 3F) |
| Compound No. 9<br>(CDCl$_3$) | 9.43 (s, 2H), 7.89 (d, 1H), 7.87 (d, 1H), 7.79 (d, 2H),<br>7.54 (s, 1H), 7.51 (t, 2H), 7.50 (d, 1H), 7.43-7.39 (m, 4H),<br>7.31 (m, 3H), 7.06 (d, 4H), 6.63 (d, 4H)<br>−77.17 (s, 3F) |
| Compound No. 10<br>(CDCl$_3$) | 8.24-8.20 (m, 8H), 7.89 (d, 1H), 7.87 (d, 1H), 7.55 (s, 1H),<br>7.50 (d, 1H), 7.41-7.37 (m, 14H), 7.33 (t, 1H), 7.30 (d, 4H),<br>7.29 (d, 4H), 7.25 (d, 4H)<br>−78.48 (s, 3F), −105.10 (s, 2F), −105.96 (s, 2F) |
| Compound No. 11<br>(DMSO-d$^6$) | 8.05 (d, 2H), 7.91 (d, 4H), 7.84 (d, 1H), 7.72 (d, 2H),<br>7.64 (d, 4H), 7.40 (t, 2H), 7.23-7.19 (m, 4H), 7.12-7.08<br>(m, 6H), 6.99 (d, 2H), 6.76 (d, 2H), 3.87 (s, 3H), 3.76 (s, 3H),<br>2.38 (s, 6H), 2.36 (s, 6H)<br>−77.28 (s, 3F) |

TABLE 2-continued

| | Upper row: 1H NMR<br>Lower row: 19F NMR |
|---|---|
| Compound No. 12<br>(CDCl$_3$) | 7.84 (d, 1H), 7.70-7.60 (m, 12H), 7.40 (t, 2H), 7.20 (t, 2H),<br>7.09 (m, 4H), 6.97 (d, 2H), 6.72 (d, 2H), 3.85 (s, 3H),<br>3.73 (3, 3H)<br>−77.85 (s, 3F) |

Evaluation Examples 1 to 11

The compounds No. 1 to No. 11 obtained in Examples 1 to 11 were subjected to elementary analysis and analysis of metal content by ICP-MASS. The results are shown in Table 3.

TABLE 3

| | Elementary Analysis<br>Upper row: Calcd./%<br>Lower row: Analyzed value/% | Metal contents/ppb | | | | |
|---|---|---|---|---|---|---|
| | | Na | Li | Ca | K | Fe |
| Compound No. 1 | C63.68, H3.80, S8.95, F7.95<br>C63.46, H3.92, S8.91, F7.87 | 250 | 154 | 13 | 61 | 16 |
| Compound No. 2 | C65.27, H4.56, S8.30, F7.37<br>C64.46, H4.80, S8.91, F7.61 | 98 | 163 | 52 | 34 | 11 |
| Compound No. 3 | C62.35, H5.32, S5.74, F5.10<br>C64.08, H5.63, S5.46, F5.00 | 165 | 178 | 41 | 55 | 22 |
| Compound No. 4 | C56.81, H3.14, S7.40, F19.73<br>C58.03, H3.46, S7.13, F18.95 | 143 | 11 | 18 | 135 | 11 |
| Compound No. 5 | C62.89, H3.96, S12.91, F5.74<br>C63.12, H4.02, S12.75, F5.25 | 102 | 150 | 30 | 51 | 21 |
| Compound No. 6 | C60.49, H4.97, S13.46, F5.98<br>C63.01, H4.79, S13.56, F5.48 | 232 | 90 | 24 | 68 | 27 |
| Compound No. 7 | C49.02, H3.43, S18.69, F5.54<br>C47.87, H3.35, S18.52, F5.68 | 57 | 120 | 13 | 74 | 19 |
| Compound No. 8 | C65.61, H4.06, S8.34, F7.41<br>C65.11, H4.25, S8.29, F7.24 | 110 | 140 | 12 | 121 | 20 |
| Compound No. 9 | C66.85, H3.69, S9.39, F8.35<br>C67.56, H3.52, S9.68, F8.65 | 139 | 119 | 28 | 30 | 18 |
| Compound No. 10 | C65.78, H3.26, S5.32, F11.04<br>C65.43, H3.15, S5.12, F10.98 | 95 | 110 | 82 | 79 | 120 |
| Compound No. 11 | C64.10, H4.52, S12.22, F5.43<br>C63.89, H4.53, S12.13, F5.20 | 131 | 56 | 29 | 150 | 22 |

From the results in the above-described Table 3, the aromatic sulfonium salt compound of the present invention was revealed to be extremely highly pure and useful for application to high-precision processing.

Examples 13 to 17 and Comparative Examples 1 to 3

Evaluation of Degradation by Irradiation of Light and Amount of Acid Generation

A 0.02 mmol/g solution, in acetonitrile, of each of the above-described compounds No. 1 to No. 4 and No. 12 and the comparative compounds No. 1 to No. 3 below was prepared. In a petri dish having an inner diameter of 93 mm, 5.00 g of each prepared solution in acetonitrile was placed, and the solution was exposed to the light having a wavelength of 365 nm at 0.8 mW/cm$^2$ for 5 minutes under a fluorescent lamp manufactured by TOSHIBA (FL10BL, 330 mm). Each solution after the exposure was subjected to titration with 0.05 N potassium hydroxide solution in ethanol using BTB as the indicator. The obtained titration value was corrected by subtracting a value similarly obtained by titration before the irradiation of light as the blank value, and the acid generation rate was calculated by the formula below:

acid generation rate (%)=acid titration value (mol)/
theoretical number of moles of each compound
(mol)×100

The results are shown in Table 4 below.

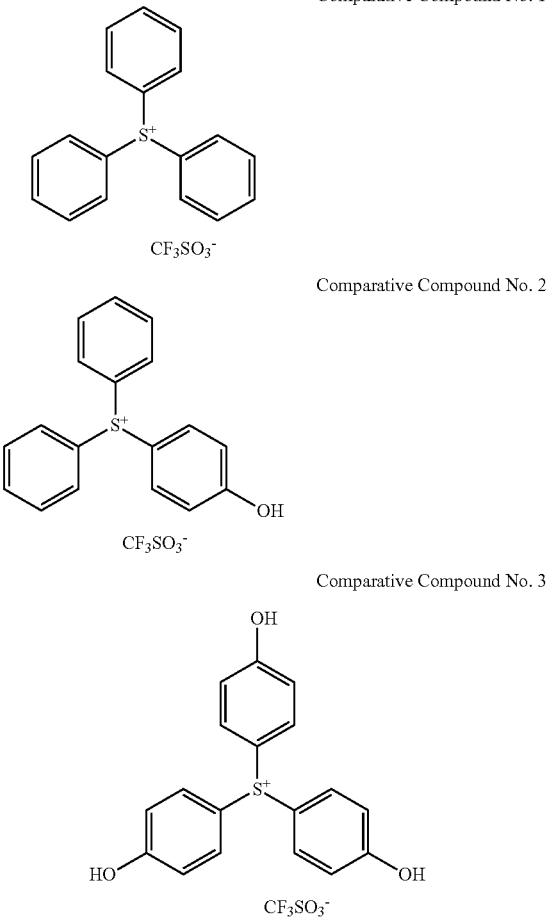

TABLE 4

| | Compound | Acid generation rate (%) |
|---|---|---|
| Example 13 | Compound No. 1 | 75 |
| Example 14 | Compound No. 2 | 64 |
| Example 15 | Compound No. 3 | 51 |
| Example 16 | Compound No. 4 | 71 |
| Example 17 | Compound No. 12 | 55 |
| Comparative Example 1 | Comparative Compound No. 1 | 0.6 |
| Comparative Example 2 | Comparative Compound No. 2 | 5.0 |
| Comparative Example 3 | Comparative Compound No. 3 | 21 |

From the results shown in the above-described Table 4, it was confirmed that the aromatic sulfonium salt compounds of the present invention have higher rates of acid generation by light compared to the comparative compounds and are better as photoacid generators.

Example 18 and Comparative Examples 4 to 6

Evaluation of Developing Property with Alkali Using Resist Composition

A 0.02 mmol/g solution, in acetonitrile, of each of the above-described compound No. 1 and comparative compounds No. 1 to No. 3 was prepared. Each solution was applied to a silicon wafer by spin coating and dried at 80° C. for 5 minutes, followed by 30 seconds of developing using 3% tetramethylammonium hydroxide solution and evaluation of the developing property. The evaluation standards were ○: absence of visible residues, x: presence of visible residues. The results are shown in Table 5.

TABLE 5

| | Compound | Developing property |
|---|---|---|
| Example 18 | Compound No. 1 | ○ |
| Comparative Example 4 | Comparative Compound No. 1 | x |
| Comparative Example 5 | Comparative Compound No. 2 | x |
| Example 5 | Compound No. 2 | ○ |
| Comparative Example 6 | Comparative Compound No. 3 | |
| Example 6 | Compound No. 3 | |

From the results shown in Table 5, it is clear that the aromatic sulfonium salt compound of the present invention is superior to the comparative compounds No. 1 and No. 2 in terms of the developing property. From these results, it was confirmed that the aromatic sulfonium compound of the present invention is a photoacid generator which is excellent in the developing property and has a good acid generation efficiency.

Example 19

Production and Evaluation of Cationically Polymerizable Composition

To a mixture of 80 g of 3,4-epoxycyclohexylmethyl-3,4-epoxycyclohexyl carboxylate and 20 g of 1,4-butanediol diglycidyl ether, the above-described compound No. 1 was added such that a concentration of 4 mmol is attained, and the resulting mixture was stirred sufficiently and uniformly. This was applied to aluminum-coated paper using a bar coater #3. To the resultant, the light of an 80 W/cm high pressure mercury lamp was irradiated using a light illuminator equipped with a belt conveyer. The distance between the lamp and the belt conveyer was set to 10 cm, and the line speed of the belt conveyer was set to 8 m/min.

After curing of the coating, the processed material was left to stand at room temperature for 24 hours. The coating was rubbed with a cotton swab to which methyl ethyl ketone was applied, and the coating was found not to be eroded even after reciprocating the cotton swab on the coating 200 times, so that it was confirmed that the curing had proceeded sufficiently.

The invention claimed is:
1. An aromatic sulfonium salt compound represented by the General Formula (I) below:

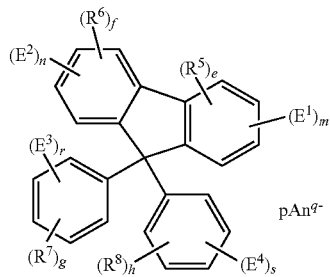

(wherein each of $E^1$ to $E^4$ independently represents a substituent represented by the General Formula (II) below or the General Formula (III) below:

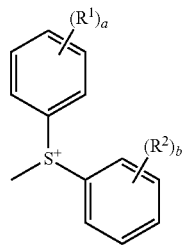

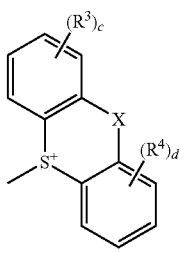

(wherein each of $R^1$ to $R^4$ independently represents hydroxyl, mercapto, a halogen atom, nitro, cyano, $C_1$-$C_{18}$ alkyl, $C_6$-$C_{20}$ aryl, $C_7$-$C_{20}$ arylalkyl, —OSiR$^{21}$R$^{22}$R$^{23}$ or —OP(=O)R$^{24}$R$^{25}$, wherein each of $R^{21}$ to $R^{25}$ independently represents $C_1$-$C_{18}$ alkyl, $C_6$-$C_{20}$ aryl or $C_7$-$C_{20}$ arylalkyl, wherein methylene groups in the above-described alkyl and arylalkyl are optionally interrupted by —O—, —CO—, —COO—, —OCO—, —OCOO—, —S—, —SO—, —SO$_2$— or —SO$_3$—, and each hydrogen atom in said alkyl, aryl and arylalkyl is optionally substituted with a halogen atom; each of a and b represents an integer of 0 to 5 and each of c and d represents an integer of 0 to 4, with the proviso that in cases where each of a to d represents a number of not less than 2, its plurality of substituents represented by $R^1$ to $R^4$ are optionally the same or different; and X represents a direct bond, an oxygen atom, a sulfur atom, CR$^9$R$^{10}$, NR$^{11}$ or carbonyl; each of $R^9$ to $R^{11}$ represents a hydrogen atom, $C_1$-$C_{18}$ alkyl, $C_6$-$C_{20}$ aryl or $C_7$-$C_{20}$ arylalkyl);
each of m, n, r and s independently represents 0 or 1 with the proviso that at least one of m and s is 1; each of $R^5$ to $R^8$ independently represents the same group as $R^1$ to $R^4$; An$^{q-}$ represents an anion having the valence of q (q represents 1 or 2); and p represents 1 or 2 which is a coefficient to maintain the neutrality of the charge).

2. The aromatic sulfonium salt compound according to claim 1, wherein, in said General Formula (I), r and s are 0.

3. The aromatic sulfonium salt compound according to claim 1, wherein, in said General Formula (I), m and n are 0.

4. The aromatic sulfonium salt compound according to claim 1, wherein, in said General Formula (I), n and r are 0.

5. The aromatic sulfonium salt compound according to claim 1, wherein, in said General Formula (I), the sum of m and s is 1.

6. The aromatic sulfonium salt compound according to claim 1, wherein, in said General Formula (I), An$^{q-}$ represents a monovalent anion which is any group selected from the group consisting of a hexafluoroantimonate ion, hexafluorophosphate ion, hexafluoroarsenate ion, tetrafluoroborate ion, hexachloroantimonate ion, perchlorate ion, trifluoromethanesulfonate ion, methanesulfonate ion, fluorosulfonate ion, difluorophosphate ion, p-toluenesulfonate ion, camphorsulfonate ion, nonafluorobutanesulfonate ion, hexadecafluorooctanesulfonate ion, tetraarylborate ion and organic fluorosulfoneimide ion.

7. The aromatic sulfonium salt compound according to claim 6, wherein said monovalent anion is trifluoromethanesulfonate ion or nonafluorobutanesulfonate ion.

8. The aromatic sulfonium salt compound according to claim 1, wherein, in said General Formula (I), $E^1$ to $E^4$ are groups represented by said General Formula (II).

9. The aromatic sulfonium salt compound according to claim 1, wherein, in said General Formula (I), both of g and h represent 1.

10. The aromatic sulfonium salt compound according to claim 1, wherein, in said General Formulae (I) to (III), at least one of $R^1$ to $R^8$ is hydroxyl.

11. The aromatic sulfonium salt compound according to claim 10, wherein, in said General Formulae (I) to (III), not less than 4 of $R^1$ to $R^8$ are hydroxyl.

12. The aromatic sulfonium salt compound according to claim 11, wherein, in said General Formulae (I) to (III), each of $R^1$, $R^2$, $R^7$ and $R^8$ represents hydroxyl; and each of a, b, g and h represents 1.

13. A photoacid generator comprising the aromatic sulfonium salt compound according to claim 1.

14. A resist composition comprising the photoacid generator according to claim 13.

15. A cationic polymerization initiator comprising the aromatic sulfonium salt compound according to claim 1.

16. A cationically polymerizable resin composition comprising the cationic polymerization initiator according to claim 15.

* * * * *